US005081020A

United States Patent [19]

Levanon et al.

[11] Patent Number: 5,081,020

[45] Date of Patent: Jan. 14, 1992

[54] EXPRESSION VECTORS CONTAINING λP$_L$ PROMOTER, T$_1$T$_2$ RRNA TERMINATION SEQUENCE, AND ORIGIN OF REPLICATION DERIVED FROM A CONSTITUTIVE HIGH COPY NUMBER PLASMID, PLASMIDS CONTAINING THE VECTORS, HOSTS CONTAINING THE PLASMIDS AND RELATED

[75] Inventors: Avigdor Levanon, Netanya; Amos B. Oppenheim; Hilla Locker-Giladi, both of Jerusalem, all of Israel

[73] Assignee: Bio-Technology General Corp., New York, N.Y.

[21] Appl. No.: 220,783

[22] Filed: Jul. 18, 1988

Related U.S. Application Data

[63] Continuation of Ser. No. 645,119, Aug. 27, 1984, abandoned.

[51] Int. Cl.$^5$ ............... C12N 15/18; C12N 15/63; C12N 15/70; C12N 15/73
[52] U.S. Cl. ............... 435/69.4; 435/320.1; 435/252.33; 935/38; 935/29; 935/60; 935/72
[58] Field of Search ............ 435/320, 69.1, 172.3, 435/252.33, 320.1, 69.4; 935/41, 42, 43, 45, 60, 73

[56] References Cited

U.S. PATENT DOCUMENTS 4,559,300 12/1985 Kovacevic et al. ......... 435/172.3 X
4,578,355 3/1986 Rosenberg ..................... 435/317
4,710,473 12/1987 Morris .......................... 435/320.1

FOREIGN PATENT DOCUMENTS 0041767 12/1981 European Pat. Off. .
0049619 4/1982 European Pat. Off. .

OTHER PUBLICATIONS

Muesing et al; Cell, vol. 24, pp. 235-242 (1981).
Seeburg et al; DNA, vol. 2, pp. 37-45 (1983).
Warburton et al., Nucleic Acids Research, vol. 11, No. 17, pp. 5837-5854 (1983).
Brosius, J., Gene 27: 161-172 (1984).

Stueber, D. et al., The EMBO Journal, vol. 1, No. 11, pp. 1399-1404 (1982).
Bernard, H. V. et al., Gene (1979), 5: 59-76.
Derom, C. et al., Gene (1982), 17: 45-54.
Gheysen, D. et al., Gene (1982), 17: 55-63.
Hedgpeth, J. et al., Mol. Gen. Genet. (1978), 163: 197-203.
Remaut, E. et al., Gene (1981), 15: 81-93.
Derynck, R. et al., Nature (1980), 287: 193-197.

(List continued on next page.)

*Primary Examiner*—Richard A. Schwartz
*Assistant Examiner*—S. L. Nolan
*Attorney, Agent, or Firm*—John P. White

[57] ABSTRACT

An improved vector upon introduction into a suitable host containing the thermolabile repressor C$_I$ renders the host capable of effecting expression of a desired gene. The vector is a double-stranded DNA molecule which includes in 5' to 3' order the following: the promoter and operator P$_L$O$_L$ from lambda bacteriophage; the N utilization site; a first restriction enzyme site permitting replacement of the ribosomal binding site which follows thereafter; a ribosomal binding site for transcribing mRNA; an ATG initiation codon or DNA which is converted into an ATG initiation codon upon insertion of the desired gene into the vector; a second restriction enzyme site for inserting the gene in phase with the ATG codon; a T$_1$T$_2$ rRNA transcription termination sequence; a DNA sequence which contains an origin of replication capable of autonomous production in the host of at least 400 constitutive copies of the vector; and either a gene associated with a selectable or identifiable phenotype trait manifested when the vector is present in the host cell or the fragment cI$^{434}$ on which is included the gene for the repressor protein and its associated promoter and operator. The distance between the 3' end of P$_L$O$_L$ and the 5' end of the N utilization site is less than about 80 base pairs. The distance between the 3' end of the N utilization site and the 5' end of the ribosomal binding site is less than about 300 base pairs.

Plasmids have been constructed from the vectors and used to produce bovine growth hormones.

9 Claims, 24 Drawing Sheets

Oppenheim, A. B. et al., J. Mol. Biol. (1982), 158: 327–346.
Shimatake, H. et al., Nature (1981), 292: 128–132.
Courtney, M. et al., Proc. Natl. Acad. Sci. (U.S.A.) (Feb. 1984), 81: 669–673.
Lautenberger, J. A. et al., Gene (1983), 23: 75–84.
Lautenberger, J. A. et al., Science (1983), 221: 858–860.
Shatzman, A. R. et al., 14 Miami Winter Symposium (1982), abstract p. 98.
Brosius, J. et al., J. Mol. Biol. (1981), 148: 107–127.
Amann, E. et al., Gene (1983), 25: 167–178.
Gelfand, D. H. et al., Proc. Natl. Acad. Sci. (U.S.A.) (1978), 75: 5869–5873.

1. Partial NdeI
2. Fill in
3. Ligase

EXPRESSION VECTORS CONTAINING λP$_L$ PROMOTER, T$_1$T$_2$ RRNA TERMINATION SEQUENCE, AND ORIGIN OF REPLICATION DERIVED FROM A CONSTITUTIVE HIGH COPY NUMBER PLASMID, PLASMIDS CONTAINING THE VECTORS, HOSTS CONTAINING THE PLASMIDS AND RELATED

This is a continuation of application Ser. No. 645,119, filed Aug. 27, 1984, now abandoned.

BACKGROUND OF THE INVENTION

One aspect of genetic engineering involves the insertion of foreign DNA sequences derived from eucaryotic sources into *Escherichia coli* or other microorganisms. A further refinement of genetic engineering concerns inducing the resulting microorganism to produce polypeptides encoded by the foreign DNA. Production of polypeptides can be considered a two-step process, with each step including numerous substeps. The two steps are transcription and translation. To produce a polypeptide efficiently and in quantity both steps of the process must be efficient. Transcription is the production of mRNA from the gene (DNA). Translation is the production of polypeptide from the mRNA.

A critical substep of the transcription process is initiation, that is, the binding of RNA polymerase to a promoter-operator region. The sequence of deoxyribonucleotide bases which make up the promoter region may vary and thereby effect the relative efficiency of the promoter. The efficiency depends on the affinity of the RNA polymerase for the promoter.

The efficiency of translation is affected by the stability of the mRNA. Increased stability of the mRNA permits improved translation. Although the exact determinants of mRNA stability are not precisely known, it is known that mRNA secondary structure as determined by the sequence of its bases has a role in stability.

The initial substep of translation involves binding of the ribosome to a base sequence on the mRNA known as the Shine-Dalgarno sequence or the ribosomal binding site (RBS). The synthesis of polypeptides begins when the ribosome migrates along the mRNA to the AUG start codon for translation. Generally these codons are found approximately 10 bases "downstream" from the Shine-Dalgarno site. Factors which increase the efficiency of translation include those which enhance binding of the ribosomes to the Shine-Dalgarno site. It has been shown that the structure of the mRNA in the region of the Shine-Dalgarno sequence and the AUG codon and the distance between the Shine-Dalgarno sequence and the AUG codon each play a critical role in determining the efficiency of translation. Other factors which affect the efficiency of translation are premature termination and attenuation. Efficiency of translation can be improved by removing the attenuation sites.

A difficulty encountered in attempts to produce high amounts of eucaryotic polypeptides in bacterial cells involves the inability of cells producing large amounts of mRNA to grow efficiently. This difficulty can be eliminated by preventing transcription by a process known as repression. In repression genes are switched off due to the action of a protein inhibitor (repressor protein) which prevents transcription by binding to the operator region. After microorganisms have grown to desired cell densities, the repressed genes are activated by destruction of the repressor or by addition of molecules known as inducers which overcome the effect of the repressor.

Numerous reports may be found in the literature concerning the cloning of eucaryotic genes in plasmids containing the P$_L$ promoter from λ bacteriophage. (Bernard, H. V., et al., Gene (1979) 5, 59; Derom, C., et al., Gene (1982) 17, 45; Gheysen, D., et al., Gene (1982) 17, 55; Hedgpeth, J. et al., Mol. Gen. Genet. (1978) 163, 197; Remaut, E., et al., (1981) Gene 15, 81 and Derynck, R., et al., Nature (1980) 287, 193. In addition, European Patent Application No. 041,767, published Dec. 16, 1981, describes expression vectors containing the P$_L$ promoter from λ bacteriophage. However, none of these references describe the use of the C$_{II}$ ribosomal binding site.

The use of a vector containing the P$_L$ promoter from λ bacteriophage and the C$_{II}$ ribosomal binding site has been described. (Oppenheim, A. B. et al., J. Mol. Biol. (1982) 158, 327 and Shimatake, H. and Rosenberg, M., Nature (1981) 292, 128.) These publications describe the production of increased levels of C$_{II}$ protein but do not involve or describe the production of eucaryotic proteins.

Other vectors which contain the P$_L$ promoter and the C$_{II}$ ribosomal binding site have also been described (Courntey, M. et al., PNAS (1984) 81, 669–673; Lautenberger, J. A. et al., Gene (1983) 23, 75–84 and Lautenberger, J. A. et al., Science (1983) 221, 858–860). However, all of these vectors lead to the production of fused proteins which contain the amino terminal portion of the C$_{II}$ protein.

In 1982 Shatzman and Rosenberg presented a poster at the 14th Miami Winter Symposium (Shatzman, A. R. and Rosenberg, M., 14 Miami Winter Symposium, abstract p98 [1982]). This abstract provides a non-enabling disclosure of the use of a vector containing P$_L$ from λ bacteriophage, Nut and the C$_{II}$ ribosomal binding site to synthesize a "eucaryotic" polypeptioe (SV40 small T antigen is actually not a eucaryotic polypeptide but a viral protein) in an amount greater than 5% of the cell protein in an unnamed bacterial host. The operator used is not defined. Neither an origin of replication nor a gene for a selectable phenotype is identified. This system with which the vector is used is described as including certain host lysogens into which the vector can be stably transformed.

Applicants are aware of the existence of a pending U.S. patent application in the name of M. Rosenberg filed under Ser. No. 457,352 by the National Institutes of Health, Dept. of Health and Human Services, U.S.A. Portions of this application have been obtained from the National Technical Information Service, U.S. Dept. of Commerce. However, the claims are not available and are maintained in confidence. The available portions of the application have been reviewed. This disclosure is not enabling. It indicates that the host is important (p8, line 17) but fails to identify any suitable host. It further depends upon the use of a λ mutant which is not specified (p4, line 20). It indicates that the host contains lysogens (p8, line 18) unlike the present invention in which the host is not lysogenic. It mentions cloning and expression of a eucaryotic gene, monkey metallothionein gene, (p7, line 18) but does not provide details. It specifies that neither the sequence nor the position of any nucleotide in the C$_{II}$ ribosomal binding region has been altered (p3, line 27).

Pending, co-assigned U.S. patent application Ser. No. 514,188, filed July 15, 1983, describes novel vectors useful for the expression of polypeptides in bacteria. These vectors include $P_LO_L$, N utilization site for binding antiterminator N protein, ribosomal binding site, ATG codon, restriction enzyme site for inserting the gene encoding the desired polypeptide, an origin of replication and a selectable marker. In these vectors the distance between the N utilization site and the ribosomal binding site is greater than about 300 base pairs. In addition, each of these vectors contains a specific ribosomal binding site which cannot be readily replaced. These vectors were not equally useful for expression of different polypeptides.

$T_1T_2$ rRNA transcription termination sequences have been described (Brosius, J., et al., J. Mol. Biol. 148, 107 (1981)). The placement of $T_1T_2$ rRNA termination sequences at the 3' end of a procaryotic gene and the expression of such gene under the control of a promoter have been described (Amann, E., et al., Gene (1983) 25, 167; Zabeau, M., et al., The EMBO Journal (1982) 1, 1217).

European patent application no. 81304573.9, published April 14, 1982 under European publication no. 049,619, discloses the use of the $\lambda$cI857 thermoinducible repressor as a stabilizing element. The repressor is cloned on the plasmid. A $\lambda$cI90 prophage defective in repressor synthesis is introduced by infection. The prophage is maintained by the cloned repressor at temperatures below 32° C. Any cell losing the plasmid will be lysed. If the temperature is increased to above 38° C., the repressor is destroyed or inactivated and the cells lyse. This stabilization system is not compatible with the vectors of the invention which include $\lambda P_L$ promoter and which express polypeptides at temperatures above 38° C.

Origins of replication from constitutive high copy number plasmids are known. For example pOP1$\Delta$6 origin of replication from ColEl has been described (Gelfand, D. H., et al., PNAS (1978) 75, (12), 5869 and Muesing, M., et al. Cell (1981) 45, 235). In addition, high copy number run-away replication plasmids, as distinguished from, constitutive high copy number plasmids, are known (Remant, E., et al. Gene (1983) 22, 103).

The present invention relates to expression vectors which unexpectedly provide enhanced expression of different polypeptides. By employing different ribosomal binding sites in the vectors of this invention it is possible to achieve enhanced expression levels of different polypeptides relative to the levels achieved with the previous vectors. In addition, using the same ribosomal binding sites as in the previous vectors, it is possible to achieve enhanced expression of the same polypeptides. Moreover, by placing $T_1T_2$ rRNA termination sequences at the 3' end of the gene encoding a polypeptide whose expression is desired, it is possible to increase the amount of desired polypeptide relative to the total polypeptide produced by a bacterial host. As importantly, the presence of the $T_1T_2$ rRNA transcription termination sequences permit origins of replication derived from constitutive high copy number plasmids to be incorporated into expression vector without loss of the ability to replicate in constitutive high copy number.

Origin of replication derived from pBR322 or non-constitutive high copy number plasmids other than runaway high copy number plasmids when incorporated into a vector are capable of producing only a certain number of copies per cell, typically less than 40 copies per cell. By substituting an origin of replication from a constitutive high copy number plasmid it has unexpectedly been found that that level of polypeptide expression is increased.

The preferred vectors of this invention are stabilized in the bacterial host and when bacteria containing plasmids which include the vectors and genes encoding polypeptides are grown, the plasmids are not lost. In this way, yield reduction caused by plasmid instability is overcome. Moreover, use of such preferred vectors avoids the use of antibiotic resistance as a selectable marker, thus permitting lower costs for producing polypeptides.

SUMMARY OF THE INVENTION

This invention concerns an improved expression vector which upon introduction into a suitable bacterial host cell, namely, *Escherichia coli*, containing the thermolabile repressor $C_I$ renders the host cell capable, upon increasing the temperature of the host cell to a temperature at which the repressor is destroyed, of effecting expression of a desired gene inserted into the vector and production of the polypeptide encoded by the gene comprising:

a double-stranded DNA molecule which includes in 5' to 3' order the following:

a DNA sequence which contains the promoter and operator $P_LO_L$ from lambda bacteriophage;

the N utilization site for binding antiterminator N protein;

a first restriction enzyme site permitting replacement of the DNA sequence containing the ribosomal binding site which follows thereafter;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a second restriction enzyme site for inserting the desired gene into the vector in phase with the ATG initiation codon; and a DNA Sequence which contains a $T_1T_2$ rRNA sequence;

and which additionally includes a DNA sequence which contains an origin of replication from a bacterial plasmid capable of autonomous replication in the host cell and production of at least 400 constitutive copies of the vector and either a DNA sequence which contains a gene associated with a selectable or identifiable phenotypic trait which is manifested when the vector is present in the host cell or a DNA sequence which contains the fragment designated cI$^{434}$, such fragment including the gene for the cI$^{434}$ repressor protein and its associated promoter and operator sequence, the distance between the 3' end of the $P_LO_L$ promoter and operator sequence and the 5' end of the N utilization site being less than about 80 base pairs and the distance between the 3' end of the N utilization site and the 5' end of the ribosomal binding site being less than about 300 base pairs. Desirably, the $T_1T_2$ rRNA termination sequence is less than about 100 base pairs from the 3' end of the second restriction enzyme site, more desirably it is less than about 20 base pairs from the 3' end of the site. Desirably the vector includes both the gene associated with the phenotypic trait and the cI$^{434}$ fragment. More desirably, the cI$^{434}$ fragment is located after the 3' end of the $T_1T_2$ rRNA termination sequence. The presently preferred origin of replication is pOPIΔ6 which is derived from a ColE1 plasmid.

Genes, e.g., cDNAs, encoding desired polypeptides, such as growth hormones, e.g., bovine, porcine, chicken or human growth hormones, human superoxide dismutase, human apolipoprotein E or analogs thereof, may be inserted into the second restriction enzyme site of the vector to create plasmids. The plasmids in turn can be introduced into suitable hosts where the genes can be expressed and the desired polypeptide produced. The presently preferred plasmids for bovine growth hormone (bGH) are p8300-10A, pSAL-170/10 and pSAL-210/4. Preferred hosts include *Escherichia coli* A1637, A1645, A2602, A2097 and A1563 if the plasmid does not contain the cI$^{434}$ fragment and A1645 (λi43-4cI$^-$miniTn10) if the plasmid contains the cI$^{434}$ fragment.

The resulting host vector systems can be employed to manufacture polypeptides, e.g., growth hormones. Host cells containing the plasmids are grown under suitable conditions permitting production of polypeptide and the resulting polypeptide is recovered.

DESCRIPTION OF THE FIGURES

The restriction maps for each of the plasmids shown in FIGS. 1-24 do not identify all restriction sites present on each plasmid. In some cases restriction sites are shown in one figure but not in another. However, in all cases those restriction sites necessary for a complete understanding of the invention are shown.

Construction of pAL500

A plasmid containing bGH cDNA, D4 (ATCC No. 31826), was digested with HaeII. The resulting 1600 base pair large fragment was purified and digested at 37° C. for 5 minutes with S1 exonuclease. A synthetic EcoRI linker with the sequence:

```
GGAATTCC
CCTTAAGG
``` was attached to the ends of the resulting fragments by ligation. The ligation mixture was cleaved with EcoRI and inserted into pBR322 (ATCC No. 37017) which had been cleaved with EcoRI. A clone, pALRI, was obtained which upon cleavage with EcoRI released a 1200 base pair fragment with the sequence:

```
AATTCCCAGCCATG ...
     GGGTCGGTAC ...
``` at the 5' end. This sequence demonstrates that pALRI contains an EcoRI restriction site which includes the TTC codon for residue number 1 (phenylalanine) of natural bGH. pALRI was subjected to a partial cleavage with PstI. The digest was treated with DNA polymerase I large fragment (Klenow) and HindIII linkers with the sequence:

```
GAAGCTTC
CTTCGAAG
``` were attached by ligation. The ligation mixture was cleaved with EcoRI and HindIII. The fragment containing bGH cDNA was isolated and subcloned into pBR322 between the EcoRI and HindIII restriction sites to give pAL500 (ATCC No.39782).

FIG. 2

Construction of pRO211 and pRO12

The plasmid pJH200 (ATCC No. 39783) was partially digested with NdeI, treated with DNA polymerase I (Klenow) to fill in the ends and the resulting ends were religated to form the expression vector pRO211. The expression vector pRO211 was digested with NdeI and HindIII, the large fragment isolated and ligated to an NdeI-HindIII bGH fragment isolated from pAL500 (ATCC No. 39782) to give pRO12. (The NdeI-HindIII fragment was produced from pAL500 by digesting it with EcoRI and ligating to the ends of the digestion product synthetic linkers with the sequence:

```
TATGGATC
ACCTAGTTAA
```

The ligation mixture was digested with NdeI and HindIII and the resulting NdeI-HindIII bGH fragment isolated.)

FIG. 3

Construction of pSAL 5200-6 pRO12 (FIG. 2) was partially digested with PvuII followed by digestion with NdeI to eliminate a 72 base pair fragment. A synthetic DNA fragment coding for the first 24 amino acids of the N-terminus of authentic bGH was ligated to the digested pRO12.

The synthetic DNA fragment was constructed by annealing two phosphorylated synthetic single-stranded DNAs of the sequence:

```
CCATATGTCCTTGTCCGGCCTGTTTGCCAACGCTGTGCTC-3'
             3'-GCGACACGAGGCCCGAGTCGTGGACGTGGTCGACG
```

The annealed fragment was treated with DNA polymerase I (Klenow) in the presence of all four deoxyribonucleoside triphosphates in order to form the full length double-stranded DNA. The fragment was digested with PvuII and NdeI before ligation to pRO12 to form pSAL 5200-6.

FIG. 4

Figure 1:
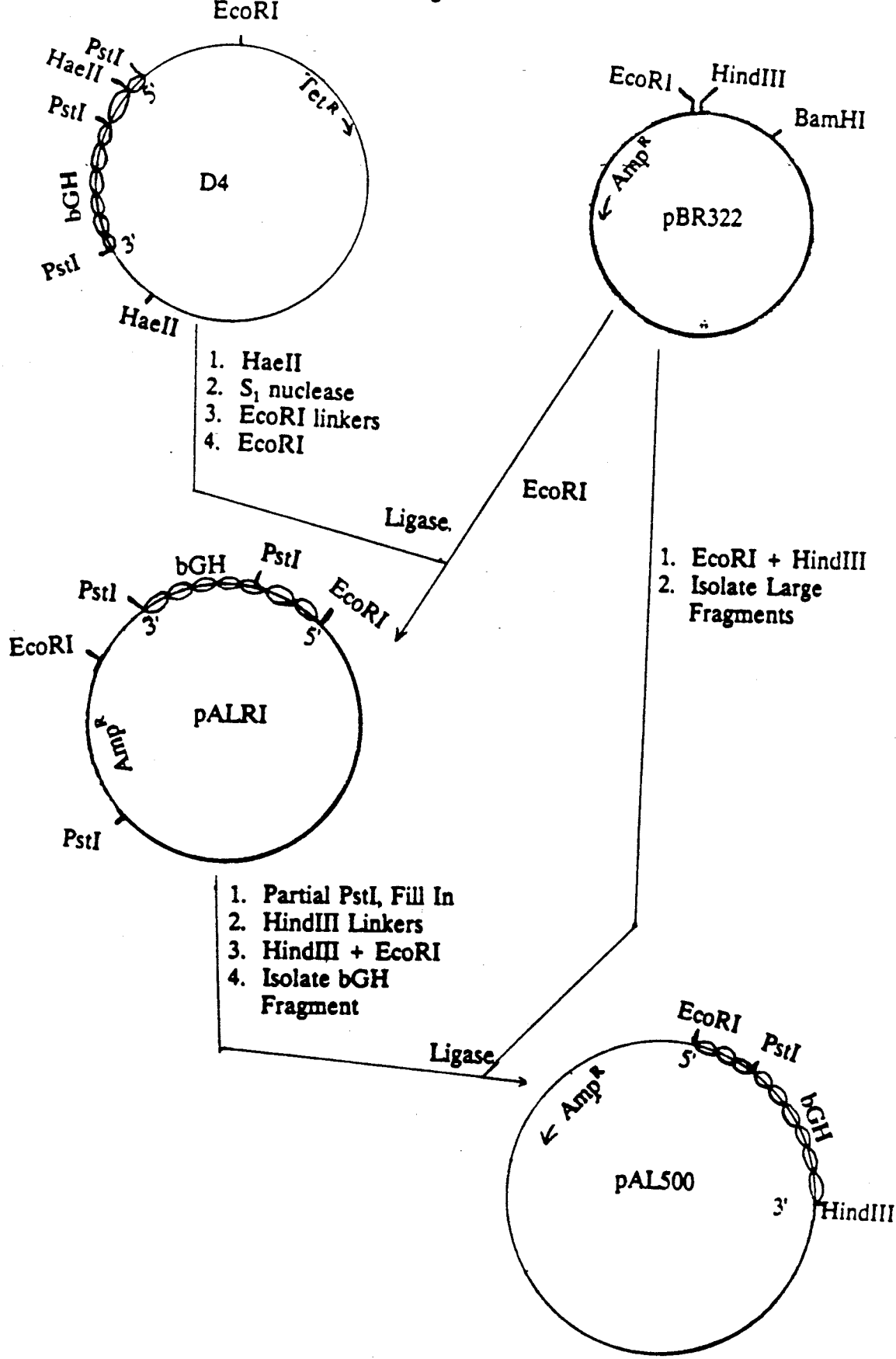
FIG. 1
Figure 2:
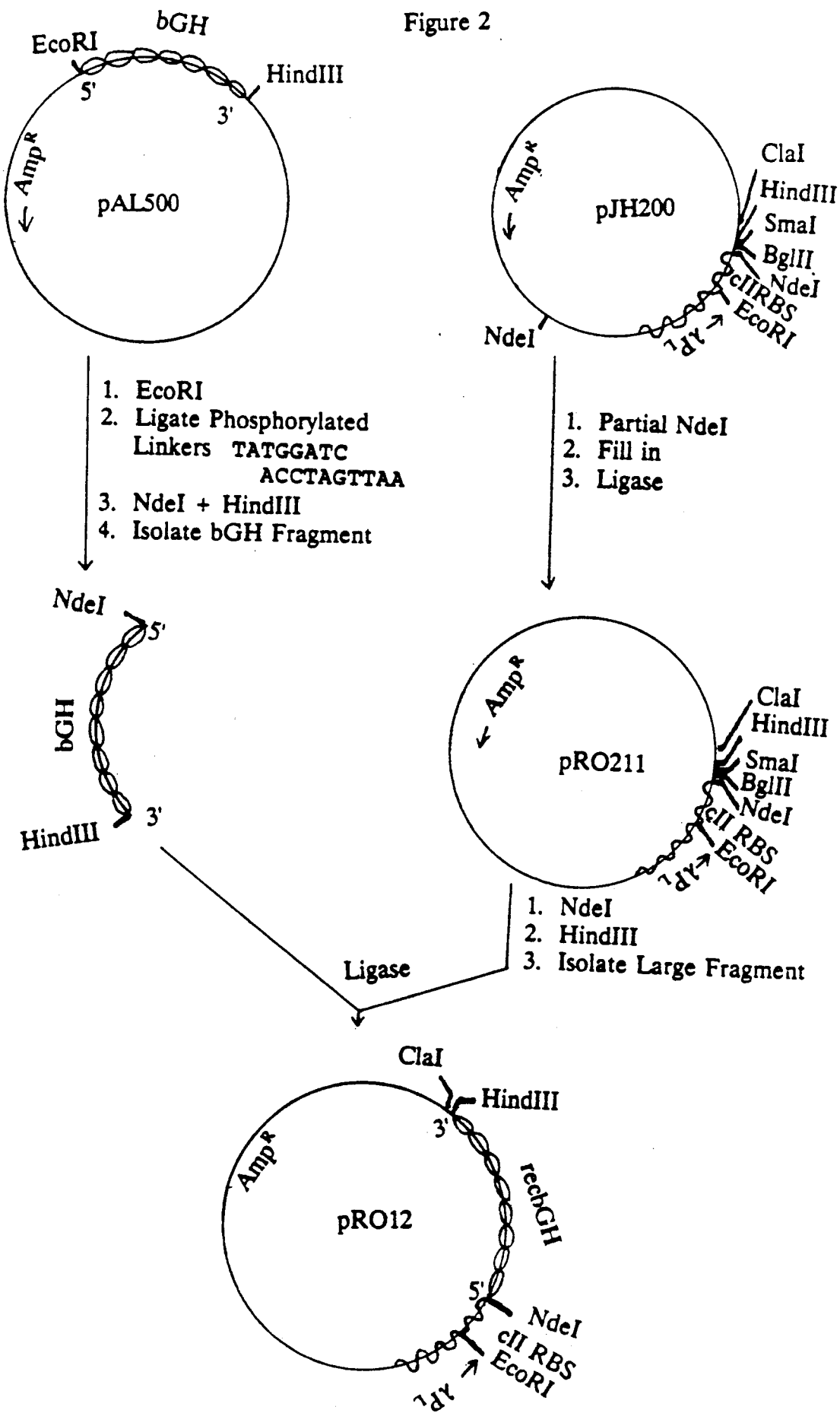

Construction of p3008 p3008 (ATCC No. 39804) was constructed by ligating NdeI-digested pRO211 [FIG. 2) with the pGH fragment isolated from an NdeI digest of the plasmid ppGH-NdeI/RI.

ppGH-NdeI/RI contains full length pGH cDNA to both ends of which NdeI sites have been added by means of synthetic linkers.

FIG. 5

Construction of p5002 p5002 was constructed by tripartite ligation of a dimerized synthetic linker and the 2 cGH fragments isolated from an NdeI and BanII digest of the plasmid pcGH-NdeI/RI. The ligation mixture was digested with NdeI and then ligated to the expression vector pRO211 (FIG. 2) after it had been restricted with NdeI. A colony containing the plasmid p5002 was isolated.

The synthetic linker was constructed from two single-stranded synthetic DNAs of the sequence TATGTTCCCTGCCATGCCCCTCTCCAACCTGTTTGCCAACGCTGTGCTGAGGGCT
ACAAGGGACGGTACGGGGAGAGGTTGGACAAACGGTTGCGACACGACTC The linker was phosphorylated before ligation. The linker codes for the first 18 amino acids of the N-terminus of the authentic cGH.

The plasmid pcGH-NdeI/RI contains full length cGH cDNA at the 5' end of which there is an EcoRI restriction site and at the 3' end of which there is an NdeI restriction site. These restriction sites were added by means of synthetic linkers.

Figure 5:
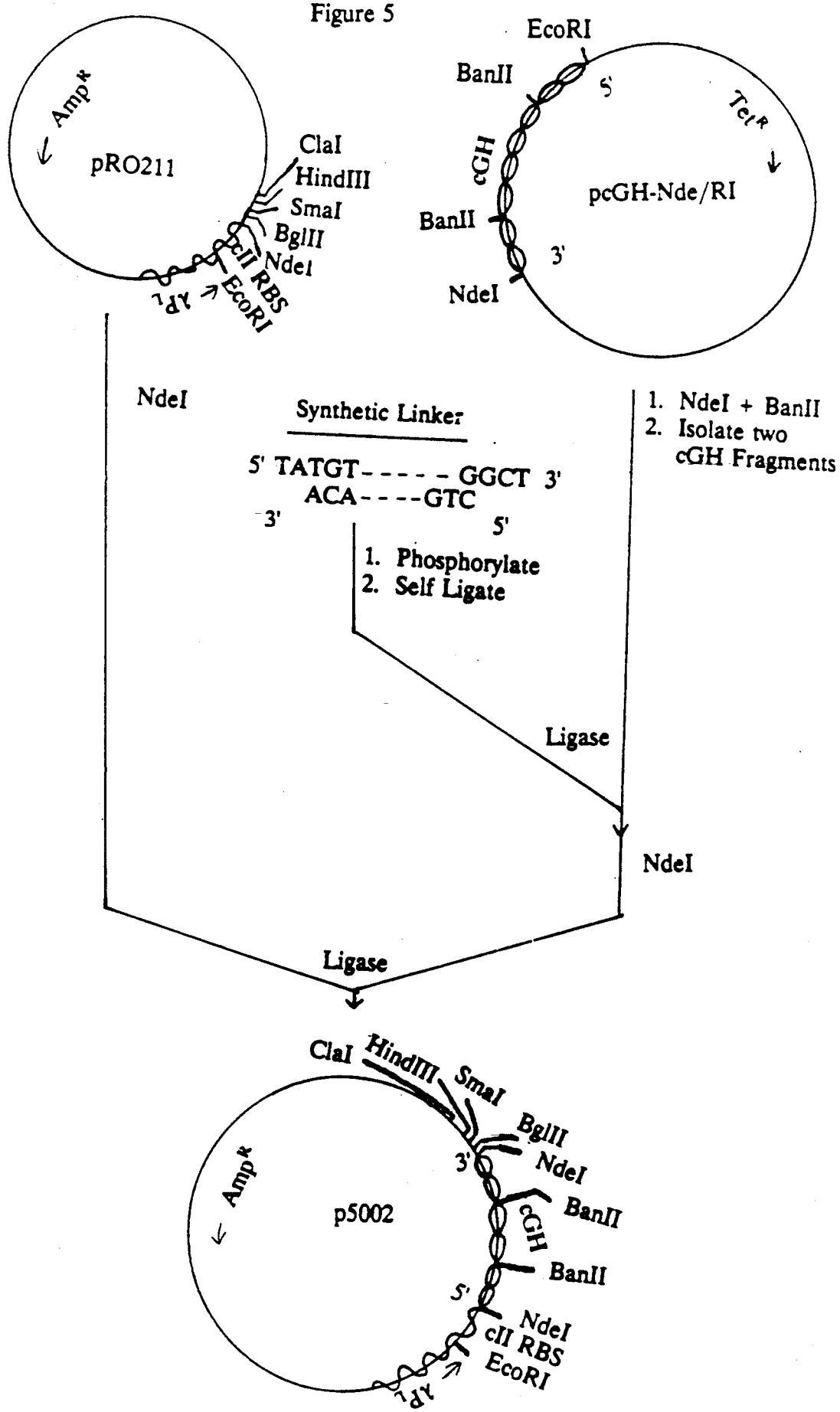

FIG. 5
Construction of pHG44 and pHG50 pRO12 (FIG. 2) was digested with HindIII. The linear form DNA (form III) was purified from agarose gel and ligated to a HindIII-HindIII fragment of about 1200 base pairs which contains the rRNA operon transcription termination sequences $T_1T_2$. The $T_1T_2$ HindIII-HindIII fragment was isolated from plasmid pPS1 (ATCC No. 39807) which had been digested with HindIII. The resulting plasmid pHG44 (ATCC No. 39806) contains the $T_1T_2$ sequences at the 3' end of the recombinant (rec) bGH sequence.

The plasmid pSK434 (ATCC No. 39784) containing the $\lambda cI^{434}$ repressor sequences was digested with HpaII. The $\lambda cI^{434}$ HpaII-HpaII fragment was isolated and ligated to pHG44 which had been digested with ClaI. The resulting plasmid pHG50 (ATCC No. 39805) contains the $T_1T_2$ transcription termination sequences and the $\lambda cI^{434}$ repressor sequence.

Figure 7:
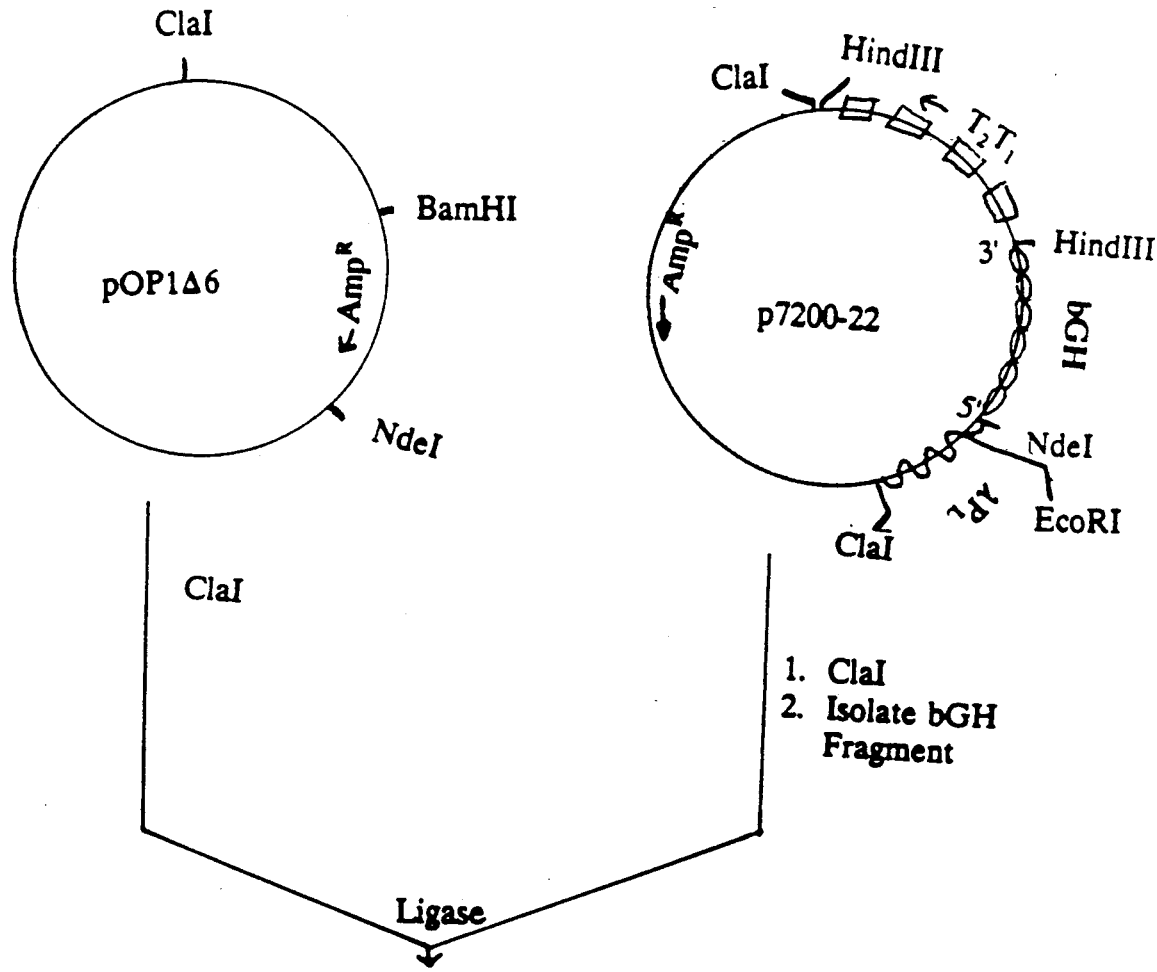
Figure 7:
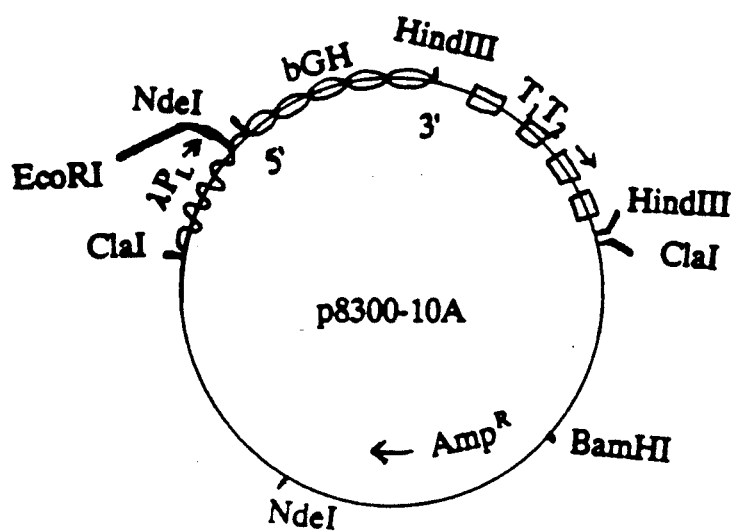

FIG. 7
Construction of p8300-10A

The plasmid p8300-10A (ATCC No. 39785) which expresses an analog of the natural phenylalanine form of bGH having methionine at the N-terminus (met—phe bGH) was prepared as follows. The plasmid p7200-22 contains the $\lambda P_L$ promoter and ribosomal binding site derived from pJH200 (ATCC No. 39783), DNA encoding met—phe bGH and the $T_1T_2$ rRNA termination sequences. ClaI—ClaI fragment containing the $\lambda P_L$ promoter, the $C_{II}$ ribosomal binding site, the met—phe bGH gene and the $T_1T_2$ transcription termination sequences was inserted into the unique ClaI site of plasmid pOP1Δ6, a constitutive high copy number plasmid, to form p830-10A.

Figure 8:
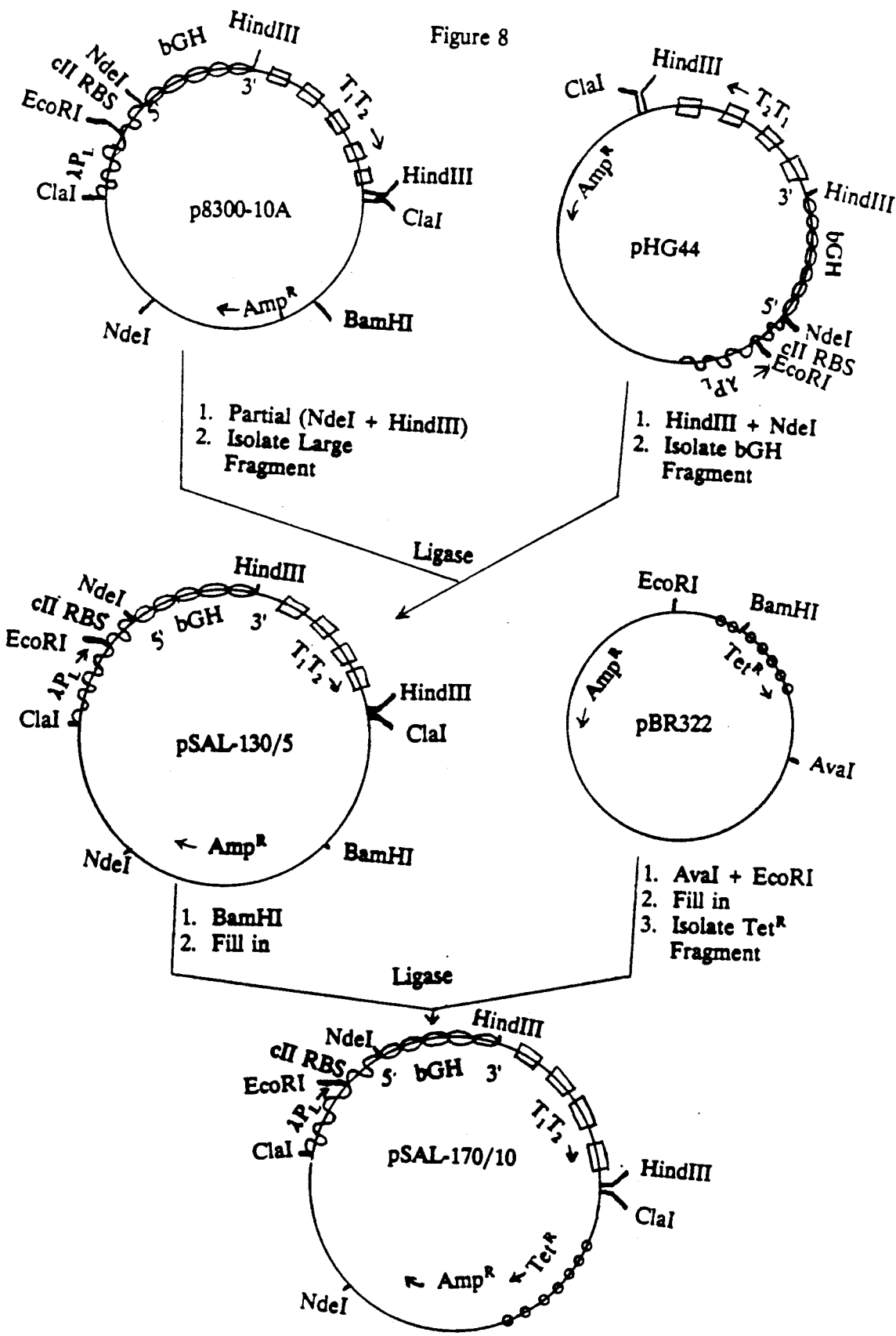

FIG. 8
Construction of pSAL-130/5 and pSAL-170/10.

The plasmid pHG44 (ATCC No. 39806) expressing met—asp—gln bGH protein was digested with NdeI and HindIII. The resulting NdeI-HindIII bGH fragment was isolated and ligated to a fragment from p830-10A (ATCC No. 39785) prepared by partial digestion with both NdeI and HindIII. Such a ligation replaces the met—phe bGH gene fragment with the met—asp—gln bGH gene fragment. The plasmid so obtained, pSAL-130/5, expresses rec bGH. pSAL-170/10 was obtained by treating the EcoRI—AvaI fragment containing the Tet ® gene of pBR322 plasmid (ATCC No. 37017) with DNA polymerase I (Klenow) and inserting it into pSAL-130/5 which had been digested with BamHI and filled in with DNA polymerase I (Klenow).

Figure 9:
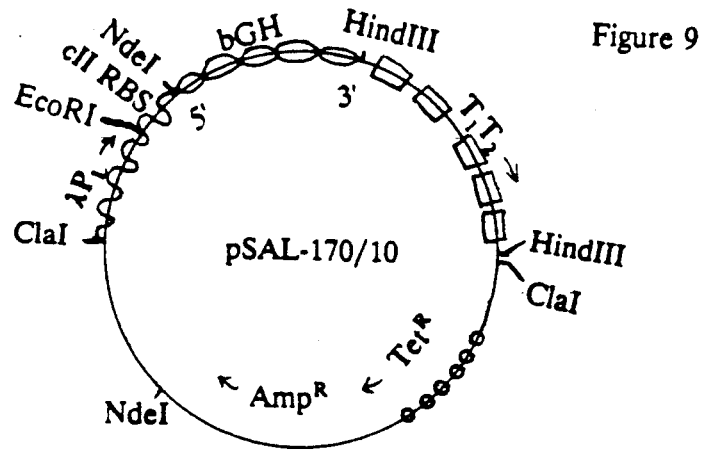
Figure 9:
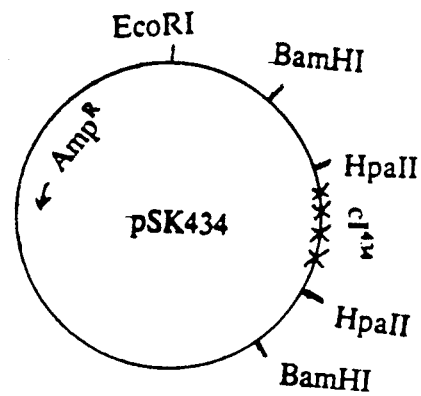
Figure 9:
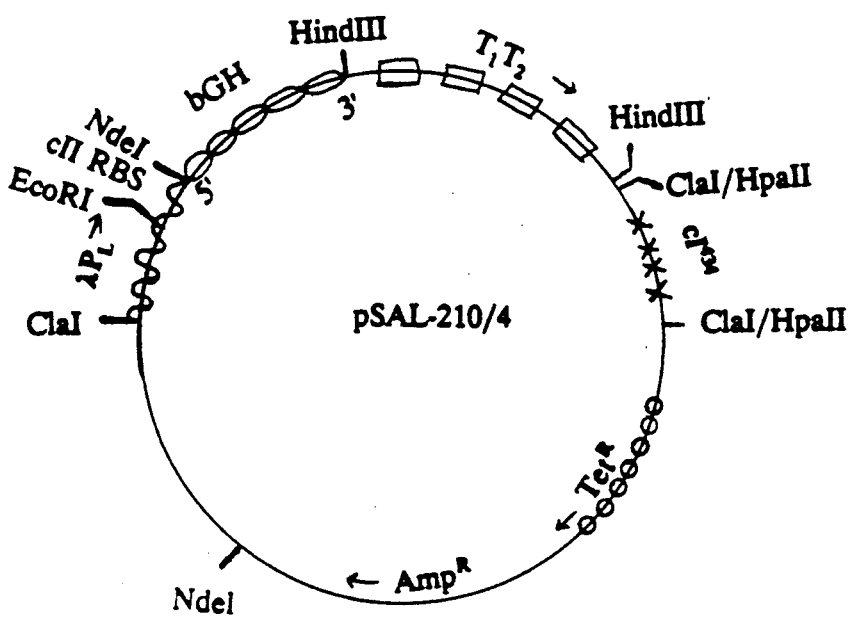

FIG. 9
Construction of pSAL-210/4

Linear form DNA (form III) was prepared by partial ClaI digestion of pSAL-170/10. It was purified from an agarose gel and ligated to a HpaII-HpaII $cI^{434}$ gene fragment which was isolated from a HpaII digest of the plasmid pSK434 (ATCC No. 39784).

Figure 3:
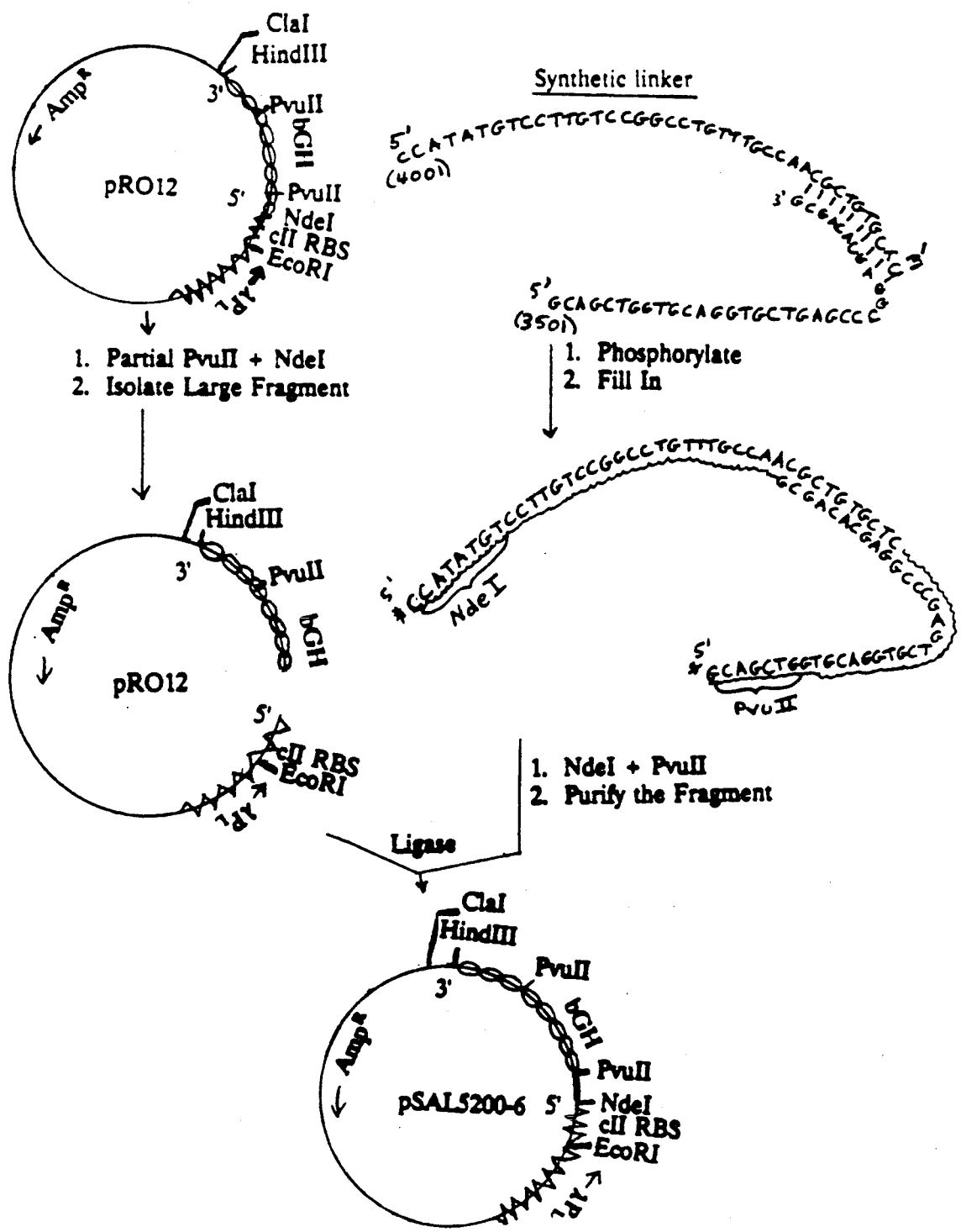
Figure 4:
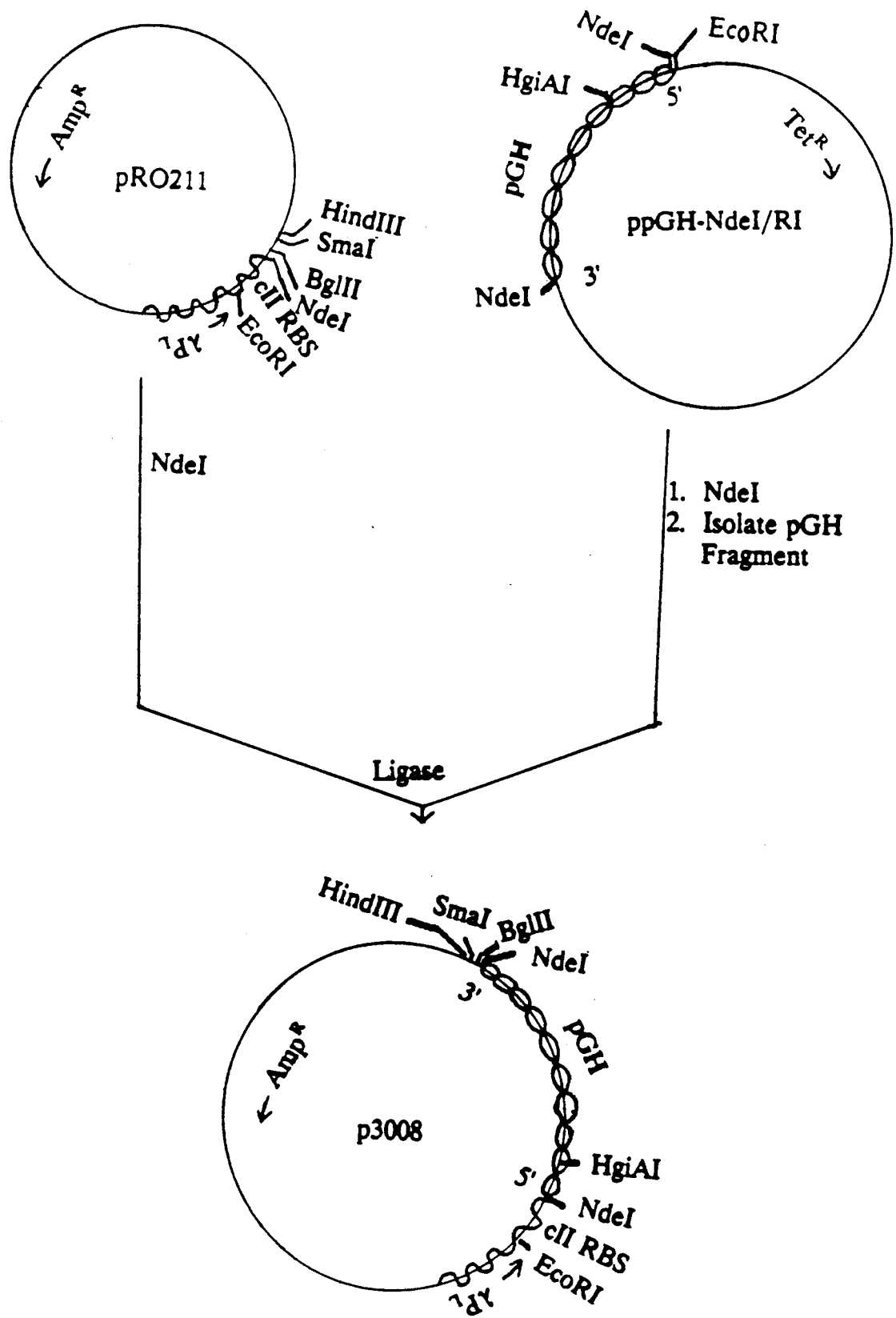
Figure 10:
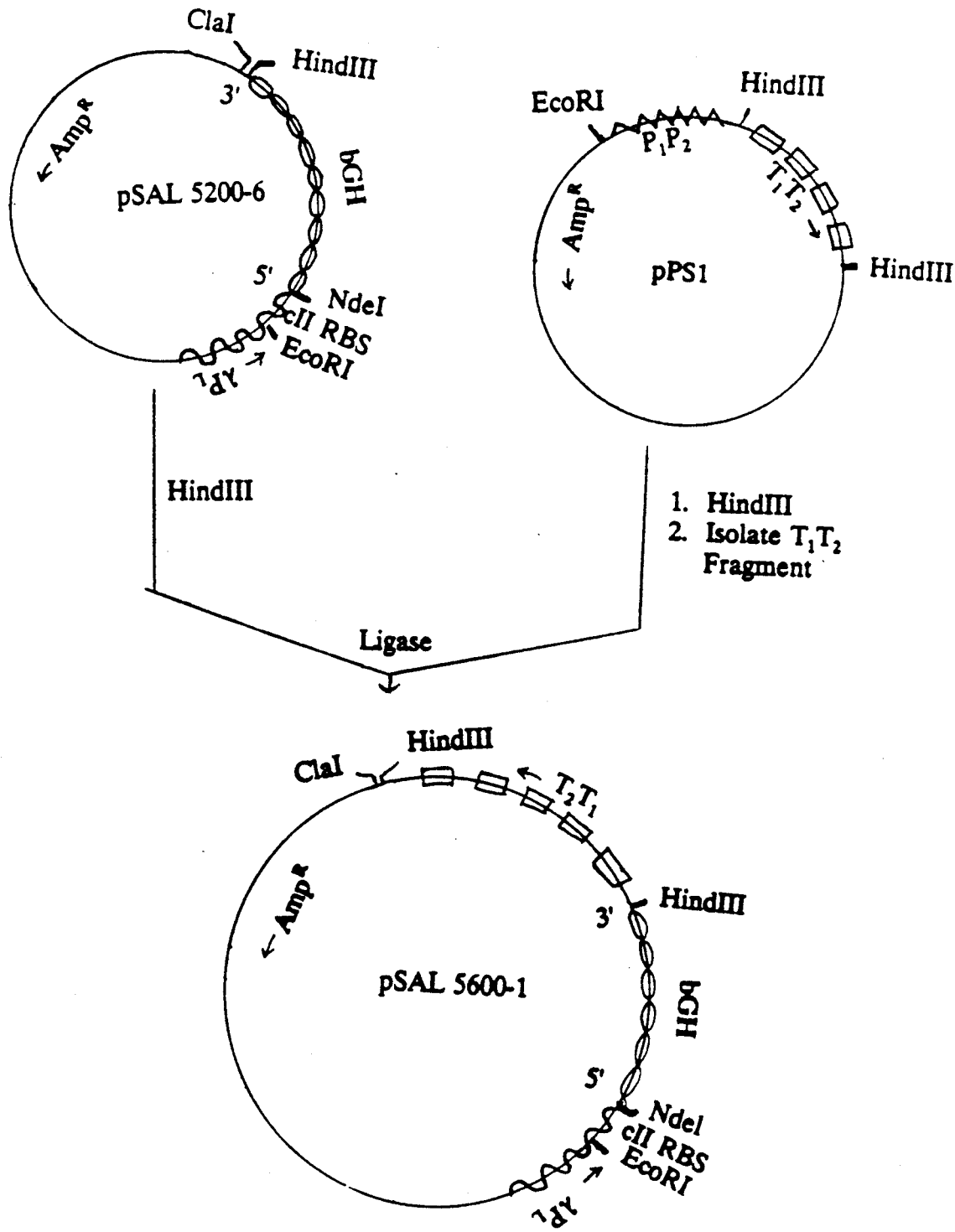

FIG. 10
Construction of pSAL 5600-1 pSAL 5200-6 (FIG. 3) was digested with HindIII. The linear form DNA (form III) was purified from an agarose gel and ligated to a HindIII-HindIII fragment of about 1200 base pairs which contains the rRNA operon transcription termination sequences, $T_1T_2$. The $T_1T_2$ HindIII-HindIII fragment was isolated from the plasmid pPS1 (ATCC No. 39807) which was digested with HindIII. The resulting plasmid pSAL 5600-1 contains the $T_1T_2$ sequences at the 3' end of the met—asp—gln bGH sequence.

Figure 11:
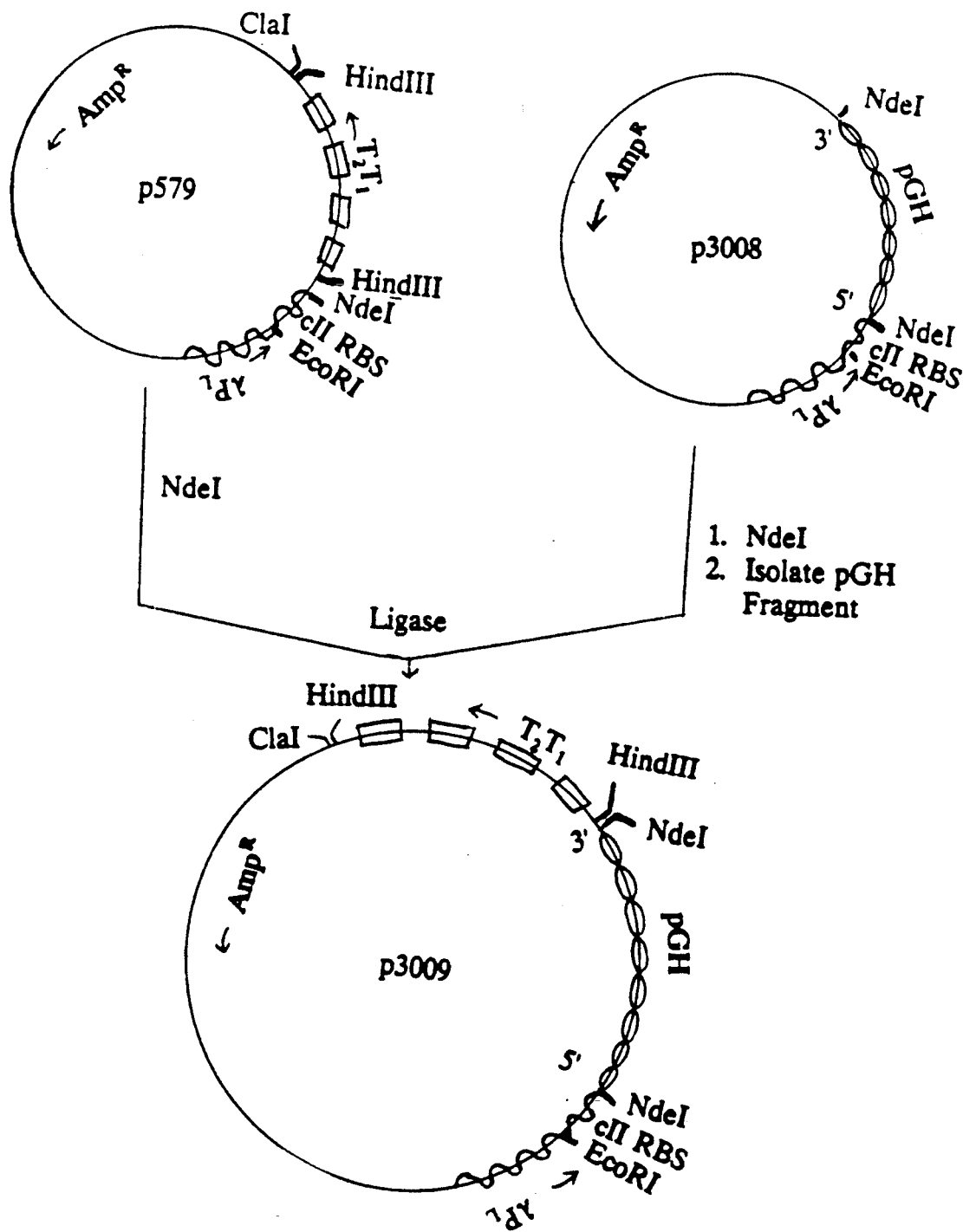

FIG. 11
Construction of p3009

Figure 19:
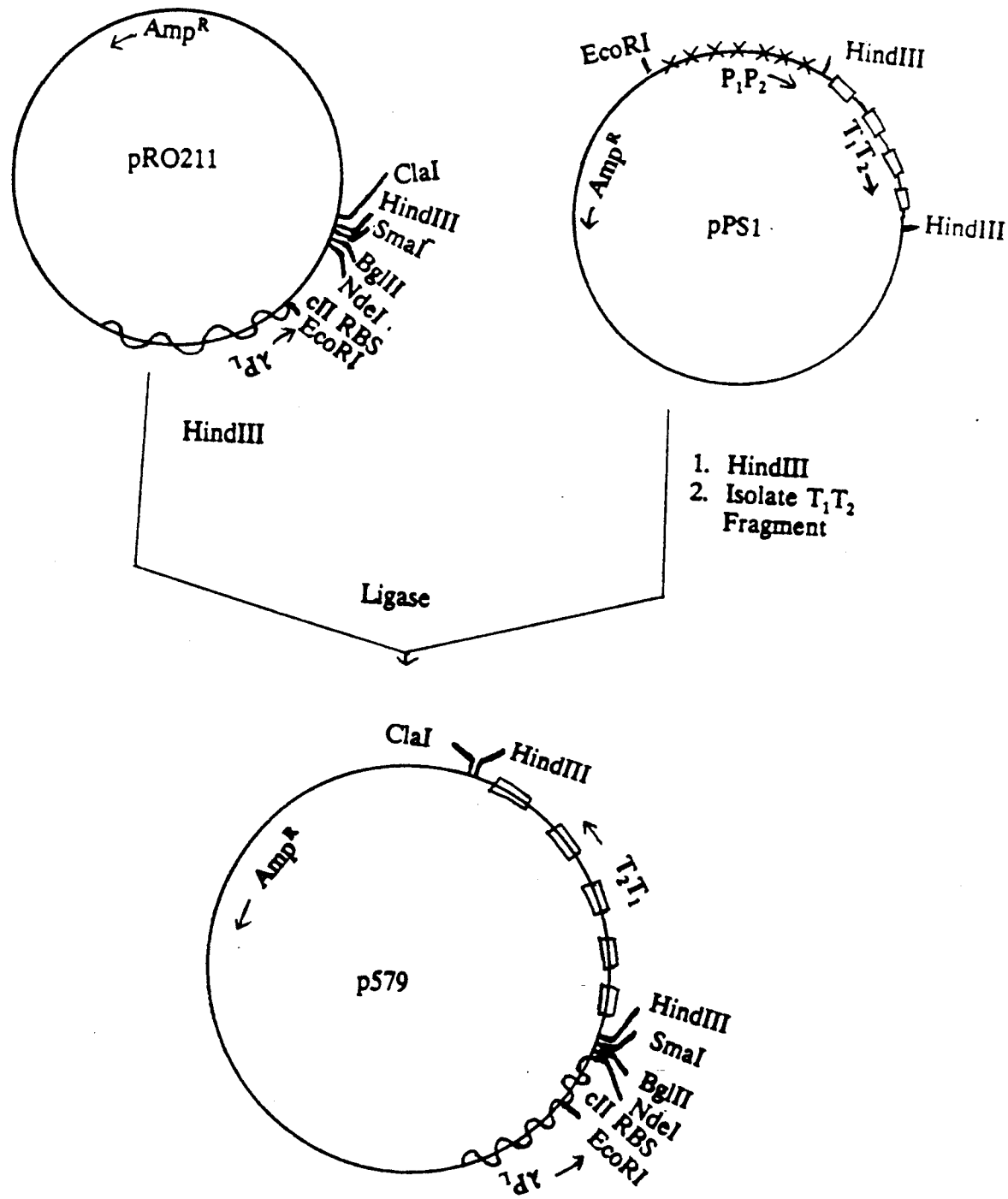

The NdeI-NdeI pGH fragment was isolated from plasmid p3008 (ATCC No. 39804) (FIG. 5). The fragment was inserted into the unique NdeI site of the expression vector p579 (FIG. 19) which had been digested with NdeI. The resulting plasmid p3009 expresses an analog of natural porcine growth hormone protein having a methionine residue added at the N-terminus.

Figure 12:
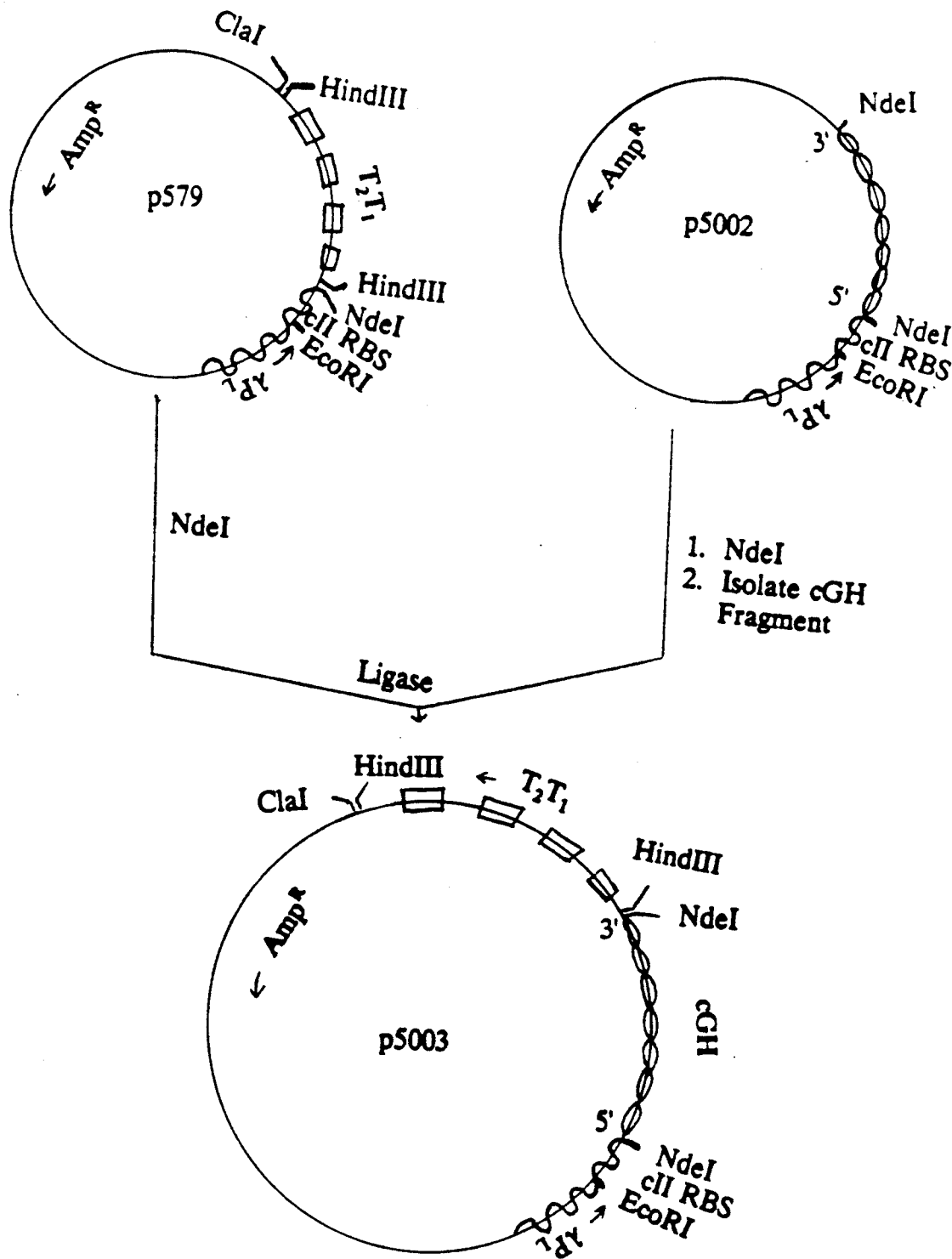

FIG. 12
Construction of p5003

The NdeI-NdeI cGH fragment was isolated from plasmid p5002. The fragment was inserted into the unique NdeI site of the expression vector p579 (FIG. 19) which had been digested with NdeI. The resulting plasmid p5003 (ATCC No. 39792) expresses an analog of natural chicken growth hormone protein having a methionine residue added at the N-terminus.

Figure 13:
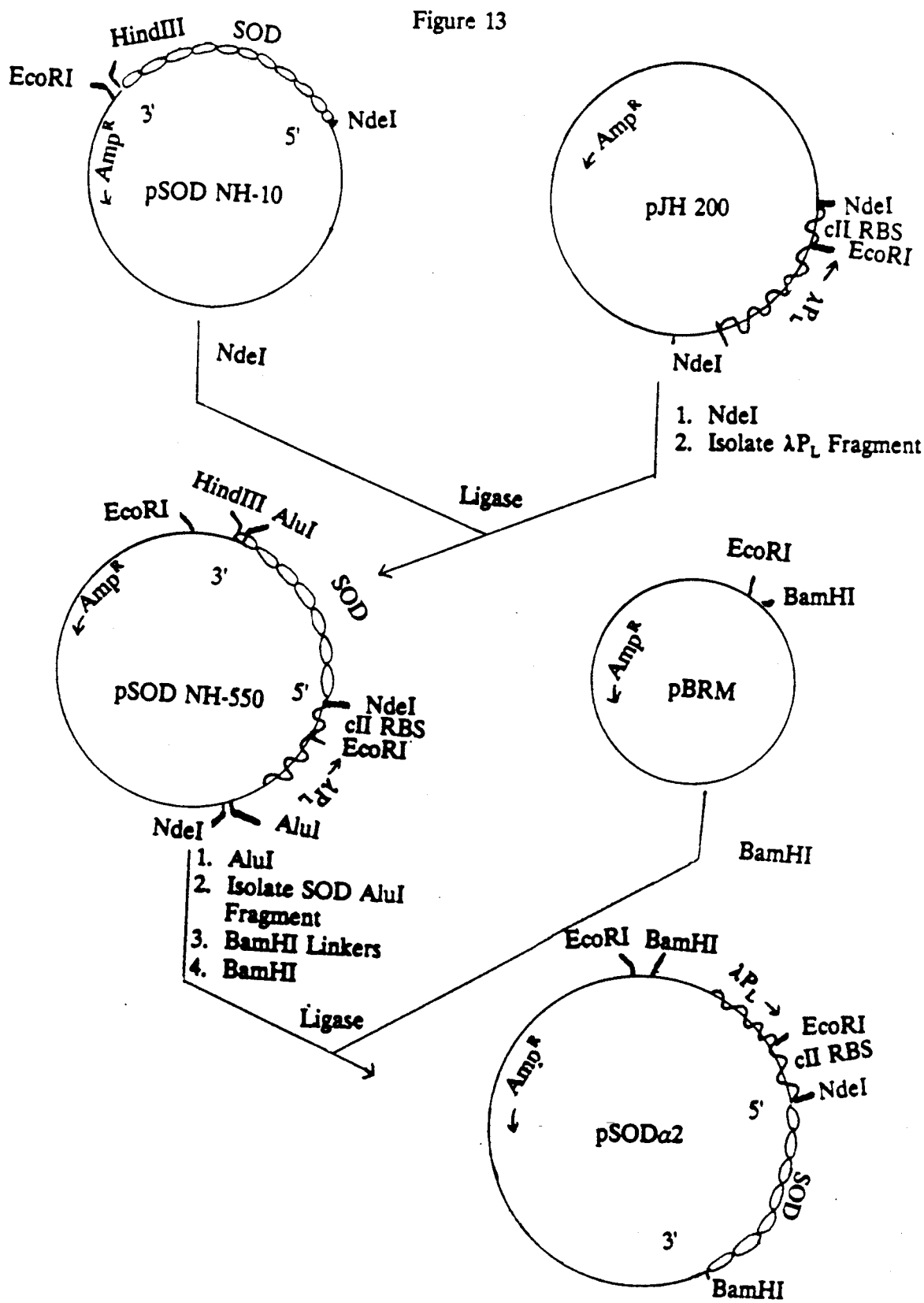

FIG. 13
Construction of pSODc2

The pJH200 (ATCC No. 39783) expression vector was digested with NdeI. The 550 base pair NdeI fragment containing the $\lambda P_L$ promoter and $C_{II}$ ribosomal binding site was isolated and inserted into the unique NdeI site of plasmid pSOD NH-10 which had been digested with NdeI. (Plasmid pSOD NH-10 is derived from a cDNA clone of human SOD [Lieman-Hurwitz, J., et al., PNAS (1982) 79:2808]) The resulting plasmid pSOD NH-550 was digested with AluI. (Only the relevant AluI site is shown in the figure.) The large AluI fragment containing the $\lambda P_L$ promoter and the SOD gene was isolated. BamHI linkers were attached and the resulting fragment was digested with BamHI. The BamHI digestion product was inserted into the unique BamHI site of pBRM (ATCC No. 37283) to form pSO-Dα2 (ATCC No. 39786).

FIG. 14

Construction of pSODo13 and pSODβ1

The plasmid pSODα2 (ATCC No. 39786) was partially digested with EcoRI and the resulting linear form DNA was isolated from an agarose gel. The purified DNA was filled in with DNA polymerase I (Klenow) and religated. The resulting clone pSODα13 contains one EcoRI site located at the 5' end of the ribosomal binding site. A fragment containing the β-lactamase promoter and ribosomal binding site was isolated from plasmid pBLA11 (ATCC No. 39788) which had been digested with EcoRI and AluI. The 200 base pair fragment was ligated to the large fragment isolated from pSODα13 which had been digested with NdeI, filled in with DNA polymerase I (Klenow) and then digested with EcoRI. The resulting plasmid pSOD⊕1 contains the ribosomal binding site of the β-lactamase gene and the λP$_L$ promoter.

FIG. 15

Construction of pSODβ$_1$T$_{11}$

Figure 14:
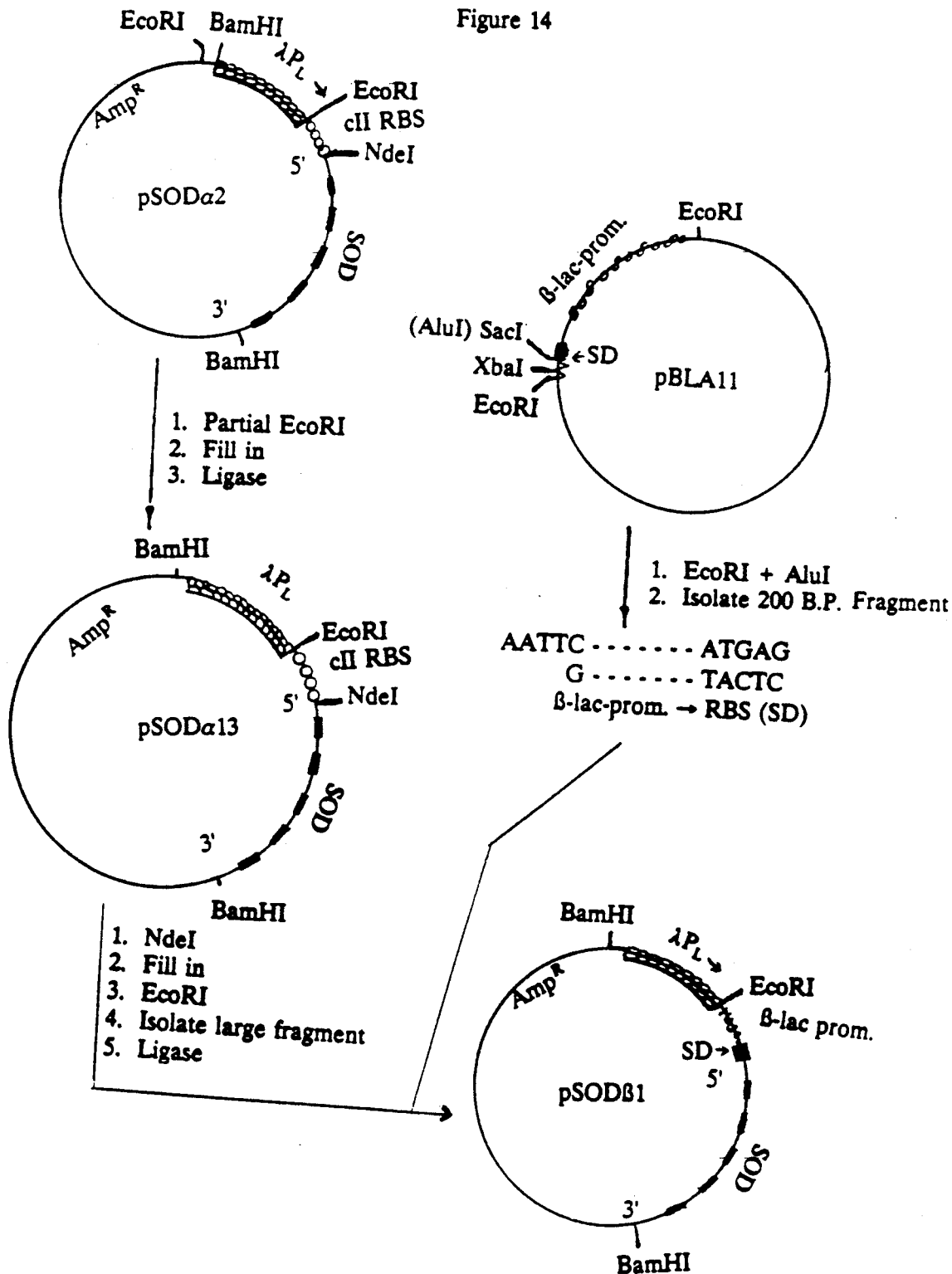

Plasmid pBR322 (ATCC No. 37017) was digested with EcoRI and AvaI. The resulting DNA was filled in with DNA polymerase I (Klenow). The Tet$^R$ gene fragment was then isolated and ligated to the large fragment isolated from pSODβ1 (FIG. 14) plasmid which had been digested with PstI followed by a partial BamHI digest and then filled in with DNA polymerase I (Klenow). The resulting plasmid pSODβ$_1$T$_{11}$ contains the TetR gene.

FIG. 16

Construction of pSODβ$_1$TT-1

The rRNA T$_1$T$_2$ transcription termination fragment was isolated from plasmid pPS1 (ATCC No. 39807) which had been digested with HindIII and filled in with DNA polymerase I (Klenow;. The fragment was ligated to plasmid pSODβ$_1$T$_{11}$ (FIG. 15) which had been partially digested with BamHI and filled in with DNA polymerase I (Klenow).

FIG. 17

Construction of pSODβ$_1$—BA2

A synthetic DNA fragment with the sequence:

```
5'-AATTCAATAATATTGAAAAAGGAAGAG-3'
   GTTATTATAACTTTTTCCTTCTCAT
``` which is similar to the sequence of the natural β-lactamase ribosomal binding site, was phosphorylated and ligated to the large fragment of pSODα13 plasmid (FIG. 14) which had been digested with NdeI and EcoRI.

FIG. 18

Construction of pTV-188

Figure 15:
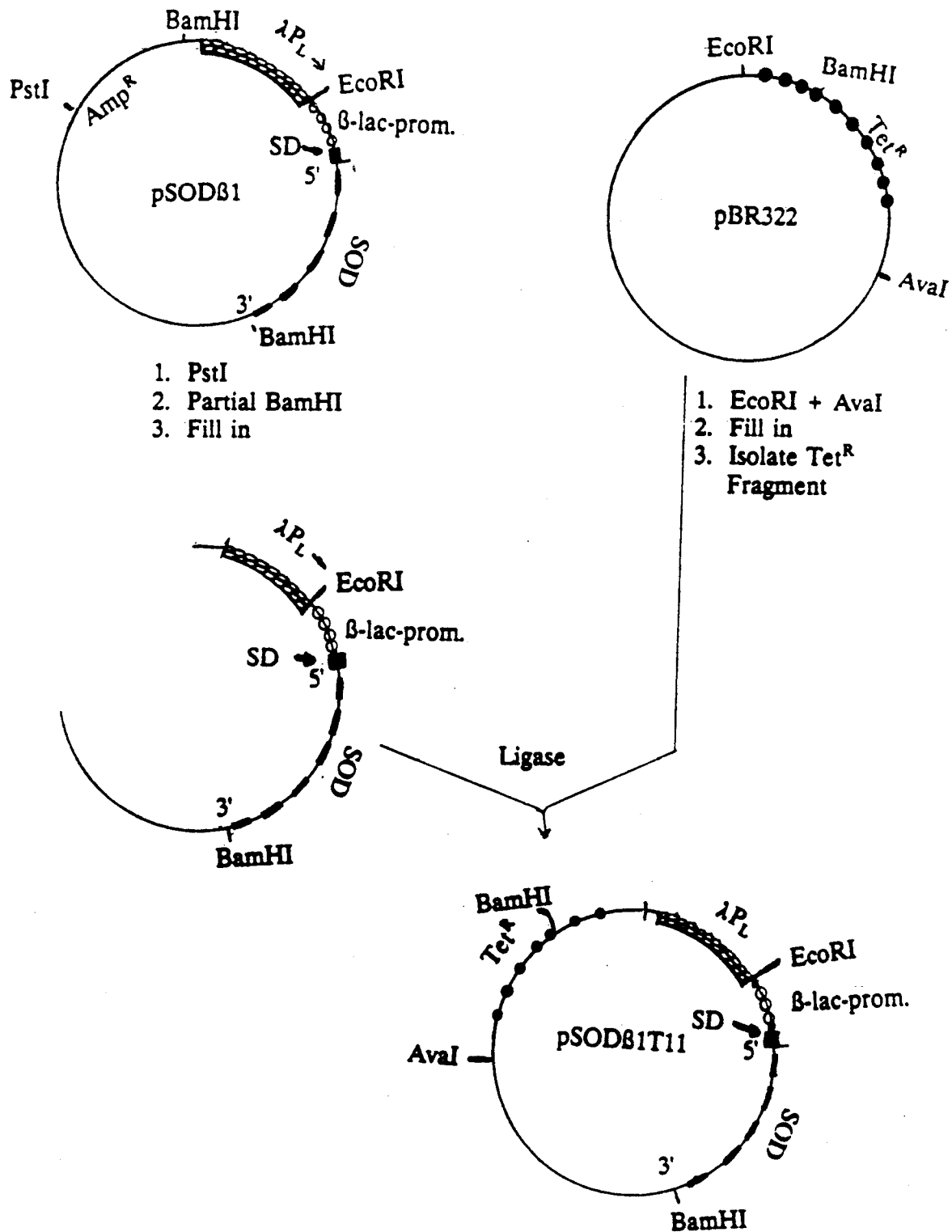
Figure 16:
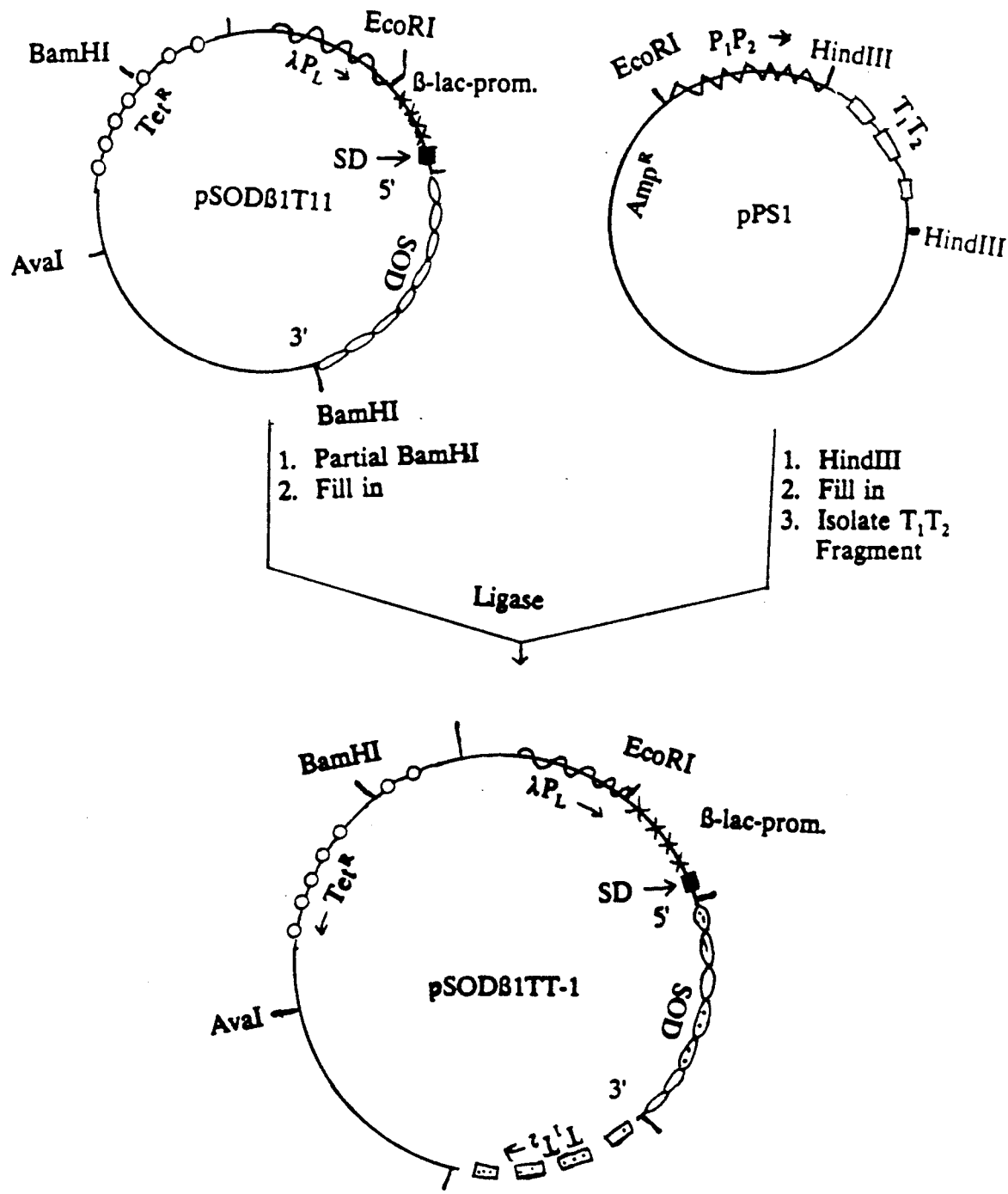
Figure 17:
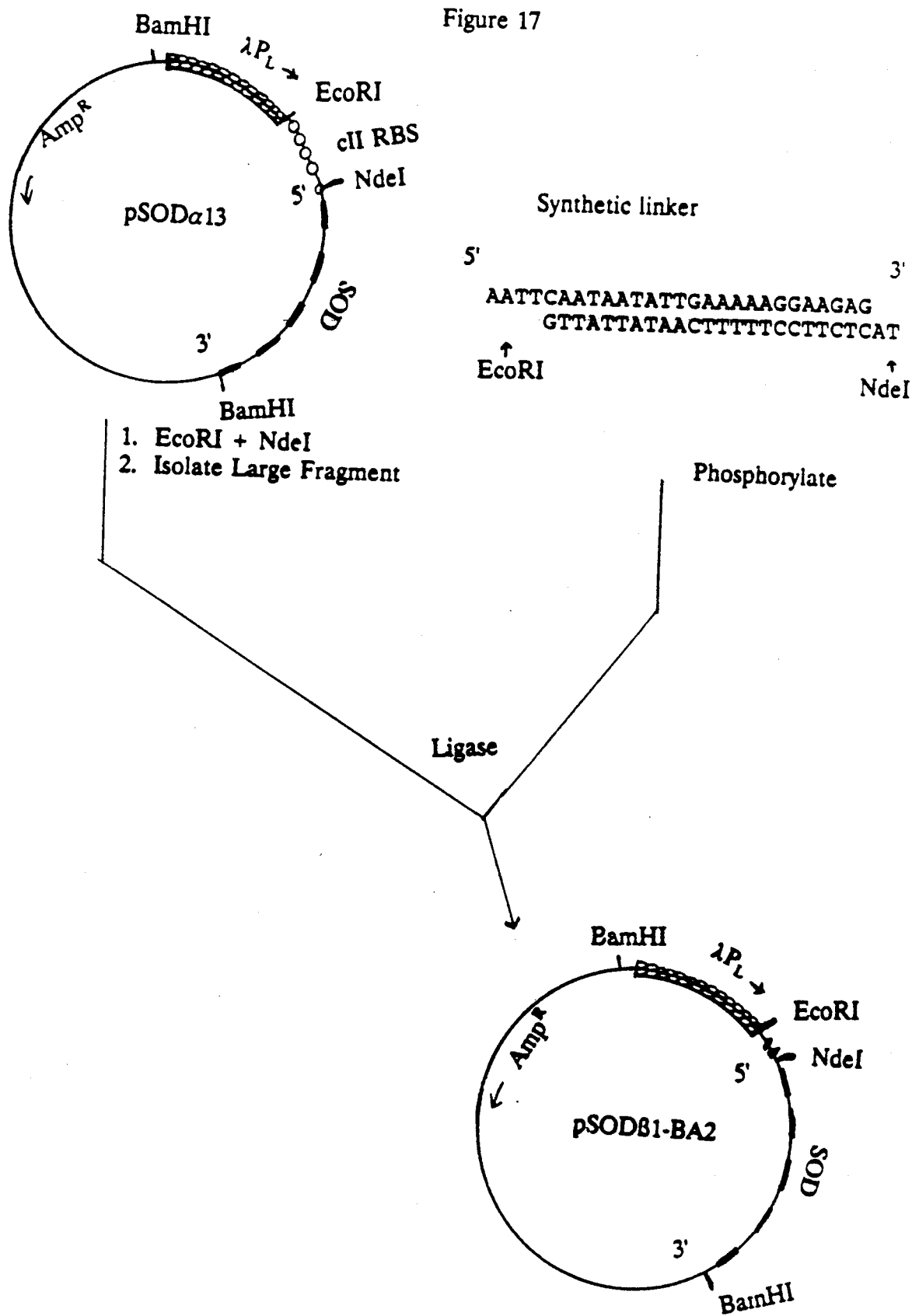
Figure 18:
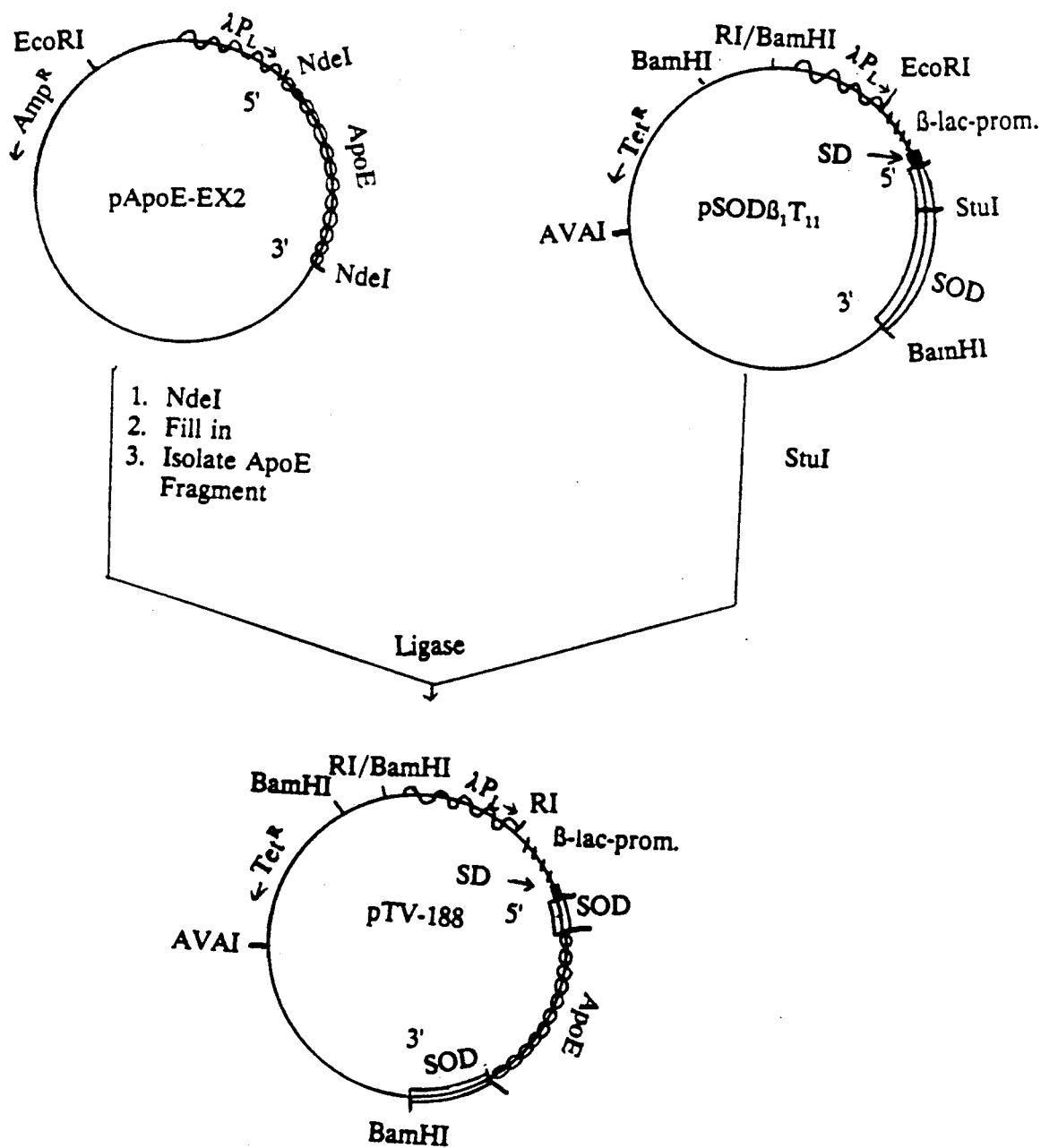

Plasmid pApoE-EX2 (ATCC No. 39787) was digested with NdeI and then fragments filled in with DNA polymerase I (Klenow). The resulting ApoE gene fragment was isolated and inserted into the unique blunt end StuI site of the pSODβ$_1$T$_{11}$ plasmid (FIG. 15). The resulting plasmid pTV-188 expresses an ApoE fused protein.

FIG. 19

Construction of p579

The rRNA operon T$_1$T$_2$ transcription termination fragment was isolated from plasmid pPS1 (ATCC No. 39807) which had been digested with HindIII. The T$_1$T$_2$ fragment was inserted into the unique HindIII site of pRO211 (FIG. 2) which had been digested with HindIII. The resulting expression vector, p579, contains the λP$_L$ promoter, the C$_{II}$ ribosomal binding site, followed by the T$_1$T$_2$ transcription termination signals.

FIG. 20

Construction of pTV-170

The NdeI-NdeI ApoE fragment was isolated from plasmid pApoE-EX2 (ATCC No. 39787) and inserted into the unique NdeI site of the expression vector p579 (FIG. 19) which had been digested with NdeI. The resulting plasmid pTV-170 expresses an analog of natural human ApoE protein having a methionine residue added at the N-terminus.

FIG. 21

Construction of pTV-190

Figure 20:
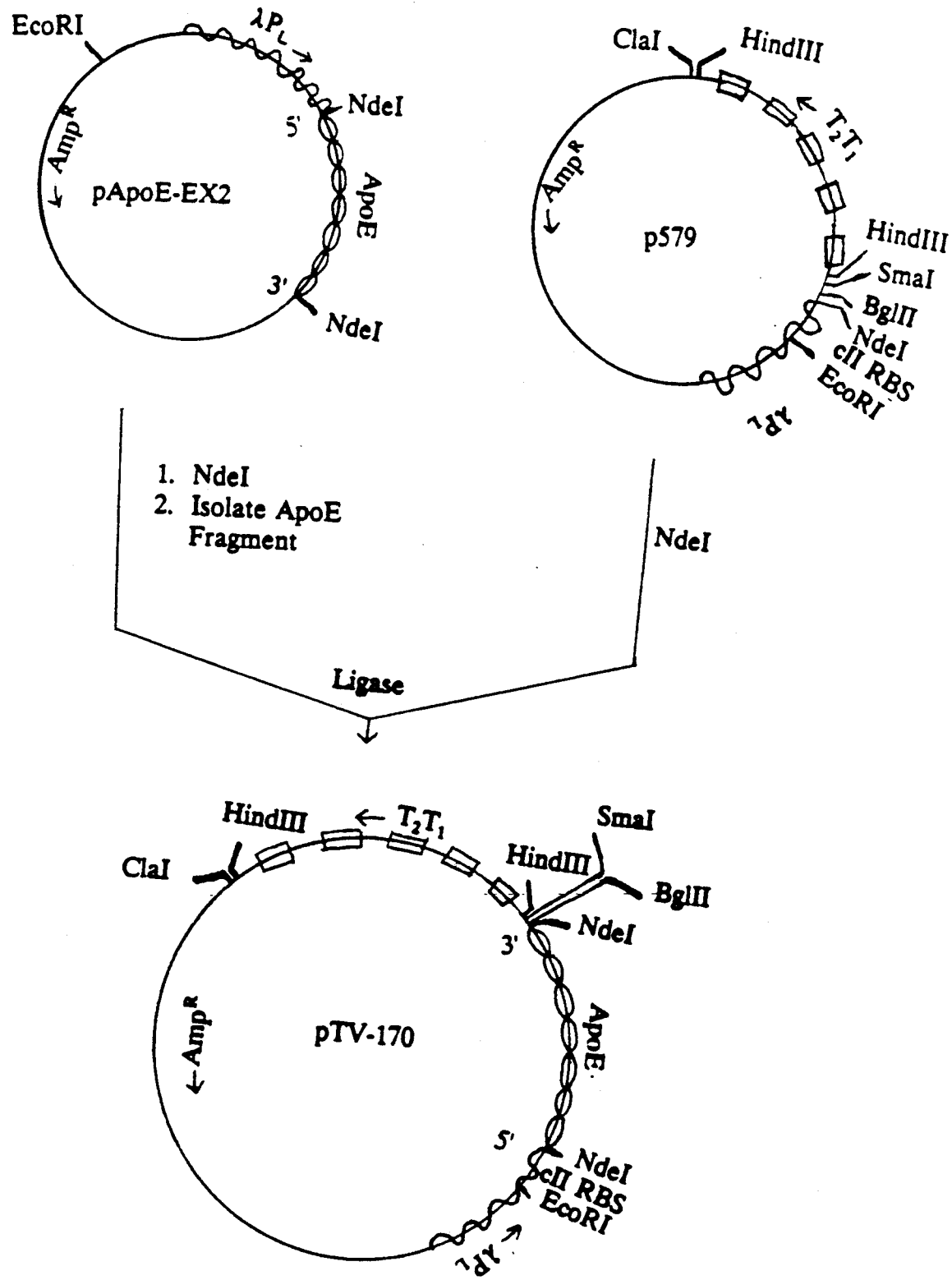

The plasmid pTV-170 (FIG. 20) was partially digested with NdeI and filled in with DNA polymerase I (Klenow). The isolated linear form DNA was religated to yield the plasmid pTV-190 which was analyzed and found to have only one NdeI site at the 5' end of the ApoE gene.

FIG. 22

Construction of pTV-194

The β-lactamase promoter and ribosomal binding site fragment was isolated from plasmid pBLA11 (ATCC No. 39788) after digestion with EcoRI and AluI. This fragment was ligated to the large fragment of pTV-170 (FIG. 20) plasmid which had been digested with NdeI, filled in with DNA polymerase I (Klenow) and then digested with EcoRI.

FIG. 23

Construction of pSAL 160-5

Figure 21:
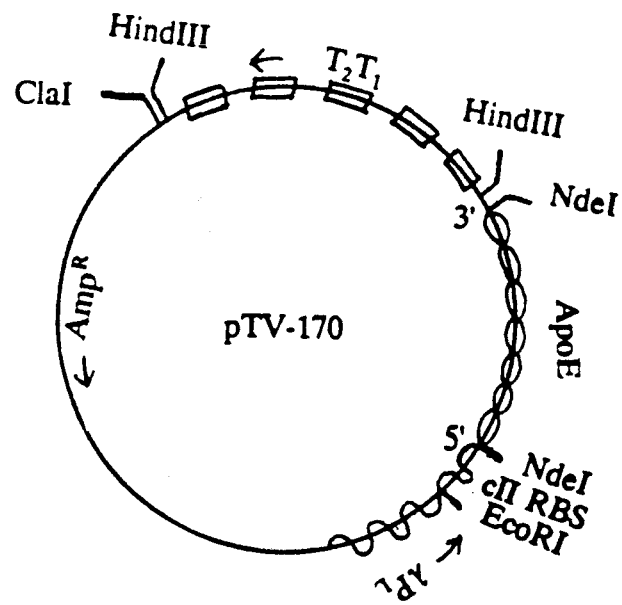
Figure 21:
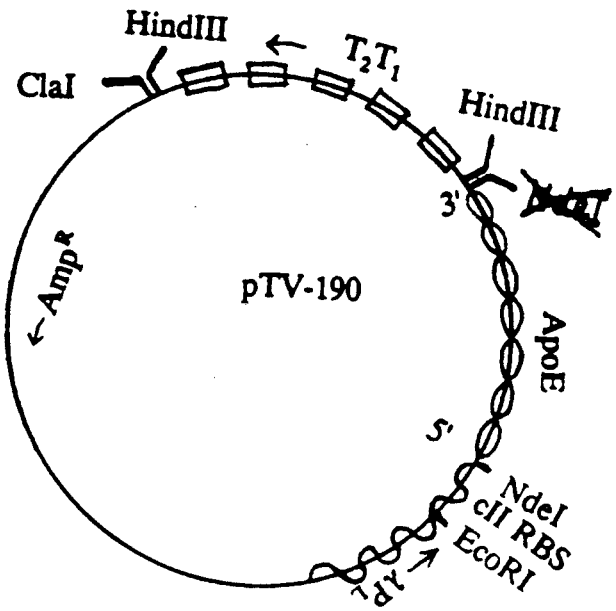
Figure 22:
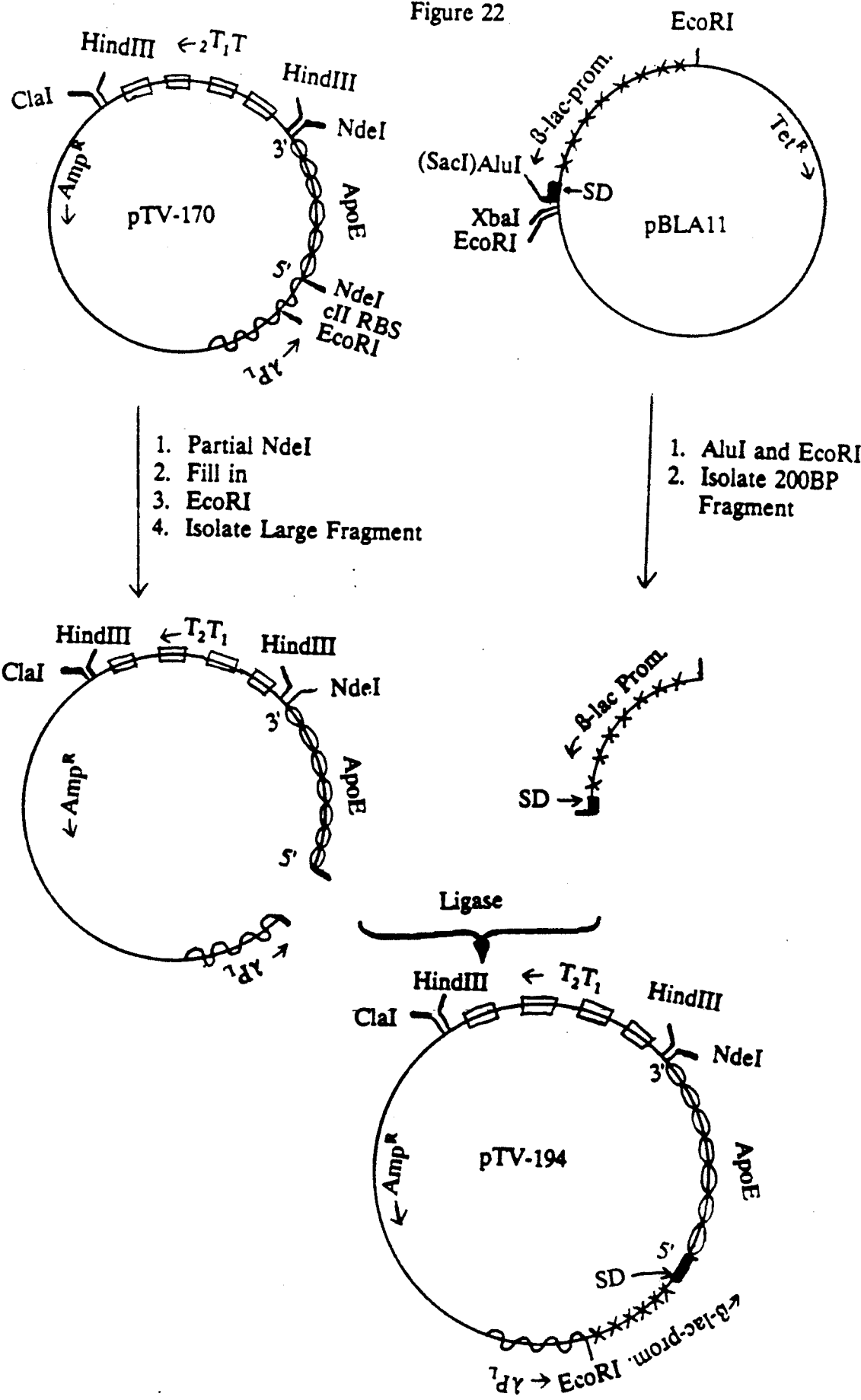
Figure 23:
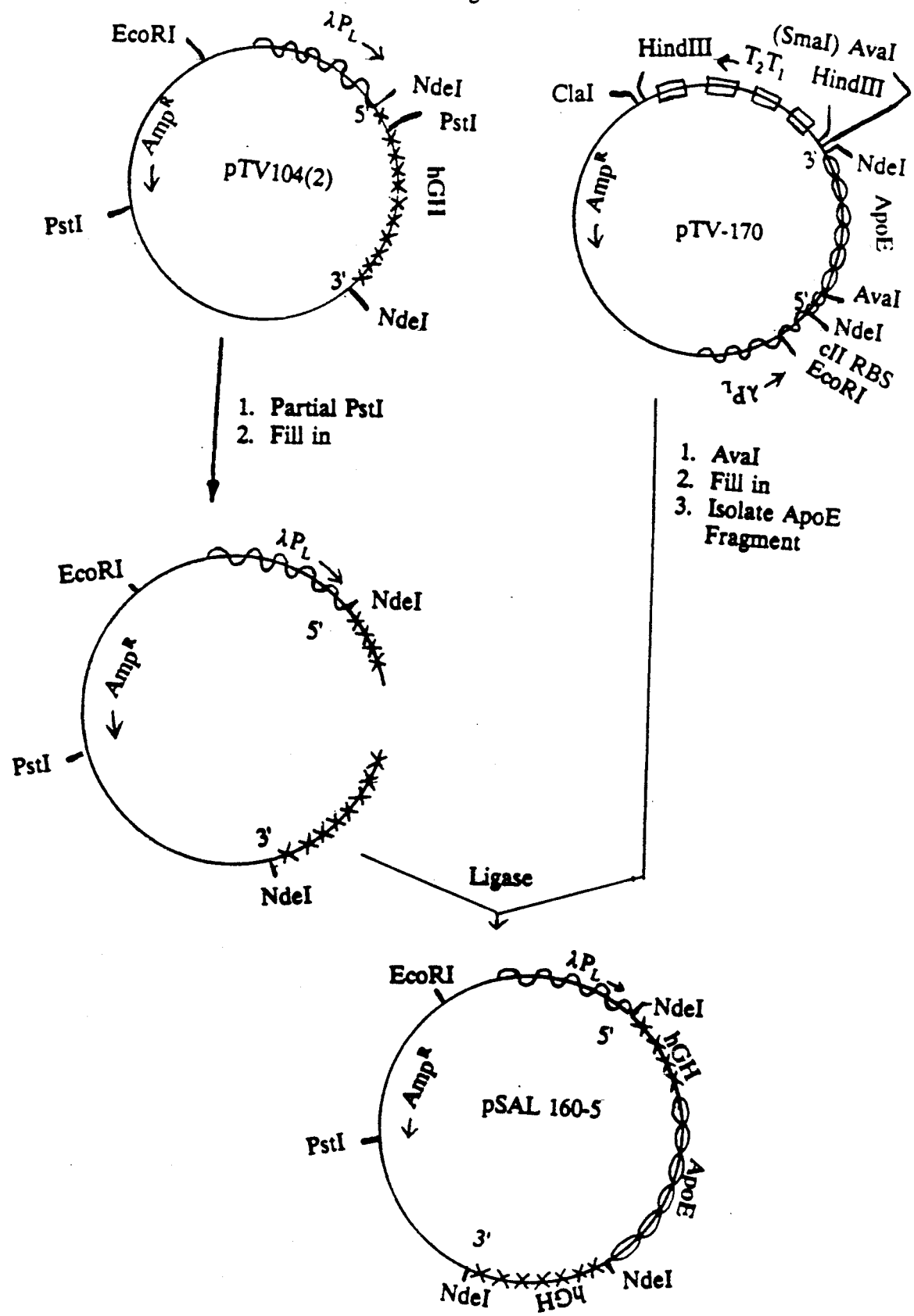
Figure 24:
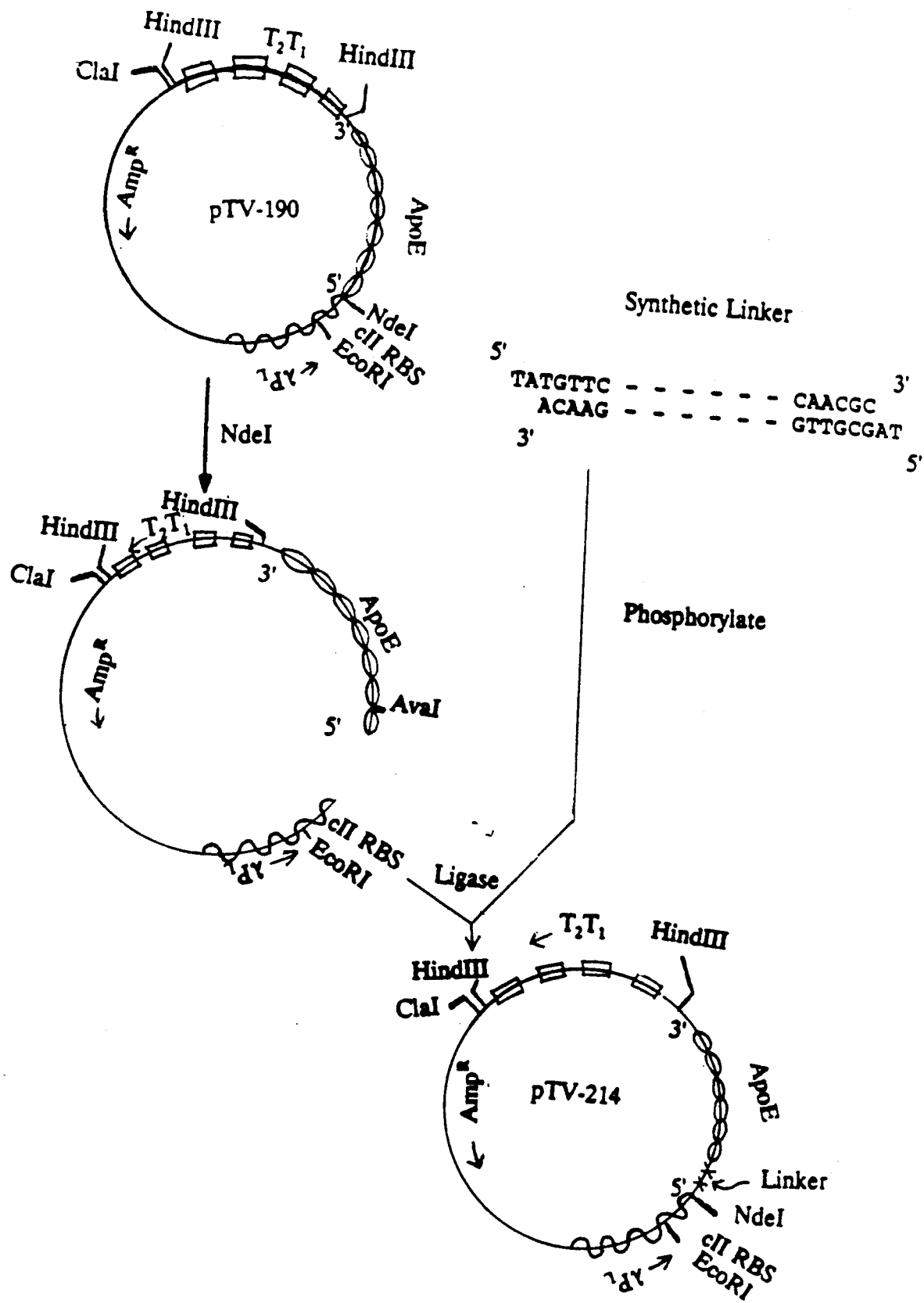

An AvaI-AvaI fragment containing the ApoE DNA sequence was isolated from pTV-170 (FIG. 21) which was digested with AvaI. The fragment was filled in with DNA polymerase I (Klenow) and isolated on agarose gel. The purified ApoE fragment was inserted into the PstI site cf the pTV 104(2) plasmid (ATCC No. 39384) which was partially digested with PstI and filled in with DNA Polymerase I (Klenow). The resulting plasmid is designated pSAL 160-5.

FIG. 24

Construction of pTV-214

A synthetic fragment containing the first 14 amino acids of human growth hormone with the sequence:

```
TATGTTCCCAACCATTCCATTATCCCGTCTGTTCGACAACGC
   ACAAGGGTTGGTAAGGTAATAGGGCAGACAAGCTGTTGCGAT
``` was phosphorylated using Y-$^{32}$P—ATP and polynucleotide kinase. The phosphorylated linker was inserted into the unique NdeI site of pTV-190 plasmid which had been digested with NdeI.

DETAILED DESCRIPTION OF THE INVENTION

A vector has been developed which enables the achievement of enhanced levels of gene expression and polypeptide production. The vector is a double-stranded DNA molecule. Upon introduction into a suitable bacterial host cell containing the thermolabile repressor $C_I$ the vector renders the host cell capable, upon increasing the temperature of the host cell to a temperature at which the repressor is inactivated, of effecting expression of a desired gene inserted into the vector and production of polypeptide encoded by the gene.

The vector includes in 5' to 3' order the following:

a DNA sequence which contains the promoter and operator $P_LO_L$ from lambda bacteriophage;

the N utilization site for binding antiterminator N protein;

a first restriction enzyme site permitting replacement of the DNA sequence containing the ribosomal binding site which follows thereafter;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a second restriction enzyme site for inserting the desired gene into the vector in phase with the ATG initiation codon; and a DNA sequence which contains a $T_1T_2$ rRNA transcription termination sequence.

The vector also includes a DNA sequence which contains an origin of replication from a bacterial plasmid capable of autonomous replication in the host cell of at least 400 constitutive copies of the vector. In addition the vector includes either a DNA sequence which contains a gene associated with a selectable or identifiable phenotypic trait which is manifested when the vector is present in the host cell or a DNA sequence which contains the fragment designated $cI^{434}$ The $cI^{434}$ fragment includes the gene for the $cI^{434}$ repressor protein and its associated promoter and operator sequence. $cI^{434}$ represses a $cI^{434-}$ lysogen; loss of the plasmid will result in cell lysis. The distance between the 3' end of the $P_LO_L$ promoter and operator sequence and the 5' end of the N utilization site is less than about 80 base pairs and the distance between the 3' end of the N utilization site and the 5' end of the ribosomal binding site is less than about 300 base pairs.

Another component of the vector is a first restriction enzyme site permitting replacement of the DNA sequence containing the ribosomal binding site which follows thereafter. Numerous such sites may be used. Suitable sites include EcoRI.

Yet another component of the vector is a second restriction enzyme site for insertion of desired genes into the vector in phase with the ATG initiation codon. Numerous such sites may be used. Suitable sites include NdeI, ClaI, HindIII, SmaI, BglII, XbaI, SacI and AluI.

Generally it is desirable that the second restriction enzyme site also function as the second restriction site necessary to permit replacement of the DNA sequence containing the ribosomal binding site. If the second restriction site is not also used for this purpose then the vector of this invention must also include a third restriction enzyme site after the ribosomal binding site but prior to the second restriction site.

A further component of the vector is a $T_1T_2$ transcription termination sequence. Preferably, the $T_1T_2$ rRNA termination sequence is less than about 100 base pairs from the 3' end of the second restriction enzyme site. More preferably, the $T_1T_2$ rRNA sequence is less than about 20 base pairs from the 3' end of the second restriction enzyme site.

Yet a further component of the vector is that it has an origin of replication from a constitutive high copy number plasmid. Preferably, this origin of replication is ColE1. More preferably, the origin is plasmid pOP1$\Delta$6 which has a restriction map shown in FIG. 7.

The vector also includes either the $cI^{434}$ repressor gene which represses a $\lambda$imm434cI$^-$ lysogen or a gene associated with a selectable or identifiable phenotypic trait which is manifested when the vector is present in the host cell or both. When the $cI^{434}$ repressor gene is contained within a the host is prevented from $\lambda$imm43-4cI$^-$ propage induction. Thus, there is no need to use expensive antibiotic selection salines when $cI^{434}$ is present.

Preferably, when the $cI^{434}$ gene is included on the vector, it is located after the 3' end of the $T_1T_2$ rRNA sequence.

Preferably, the vector contains two unique restriction enzyme sites. The first site permits replacement of the DNA sequence containing the ribosomal binding site. The second site permits insertion of the desired gene into the vector in phase with the ATG initiation codon. In a presently preferred embodiment, EcoRI is the first restriction enzyme site and NdeI is the second restriction enzyme site.

The preferred host for use with the vector is *Escherichia coli*. The presently preferred strains are A1637, A1645 (c600 r$^{-+}$gal$^+$ thr$^-$ leu$^-$ lac$^-$ Z$^-$ ($\lambda$cI857 $\Delta$H1 $\Delta$Bam N+)), A2602, A2097, A1563 and A1645 ($\lambda$i43-4cI$^-$ mini Tn10). A1645 ($\lambda$i434cI$^-$ mini Tn10) is presently the most preferred strain for expression of animal growth hormone genes. It has been deposited with the American Type Culture Collection in Rockville, Md., U.S.A. containing plasmids as described more fully hereinafter. All of the deposits were made pursuant to the Budapest Treaty on the International Recognition of the Deposit of Microorganisms except that pBR322 and pBRM are fully available from the American Type Culture Collection as ATCC Nos. 37017 and 37283, respectively, and D4 was deposited under ATCC No. 31826 in connection with the filing of a U.S. patent application.

A1645 (C600 r$^-$m$^+$ gal$^+$ *l* thr$^-$ leu$^-$ lac$^-$ Z$^-$cI$^{857}$ $\Delta$H$_1$ $\Delta$Bam N+)) was obtained from A1637 by selection for Gal$^+$ (ability to ferment galactose) as well as loss of tetracycline resistance. It still contains the lambda expression system but part of the transposon has been removed by selection.

A2602 and A1563 are derived from SA500. Their phenotypes are SA500 his$^-$ ile$^-$ gal$^+$ 8($\lambda$CI857 $\Delta$H1 $\Delta$Bam N+) and SA500 his$^-$ ile$^-$ gal$^+$ $\Delta$8 lac ZxA21 (CI859 int2 xis1 nutL3 $\Delta$H1), respectively. A2097 is derived from A1645. Its phenotype is A1645 lac $\Delta$χA21 proC:Tn10.

Figure 6:
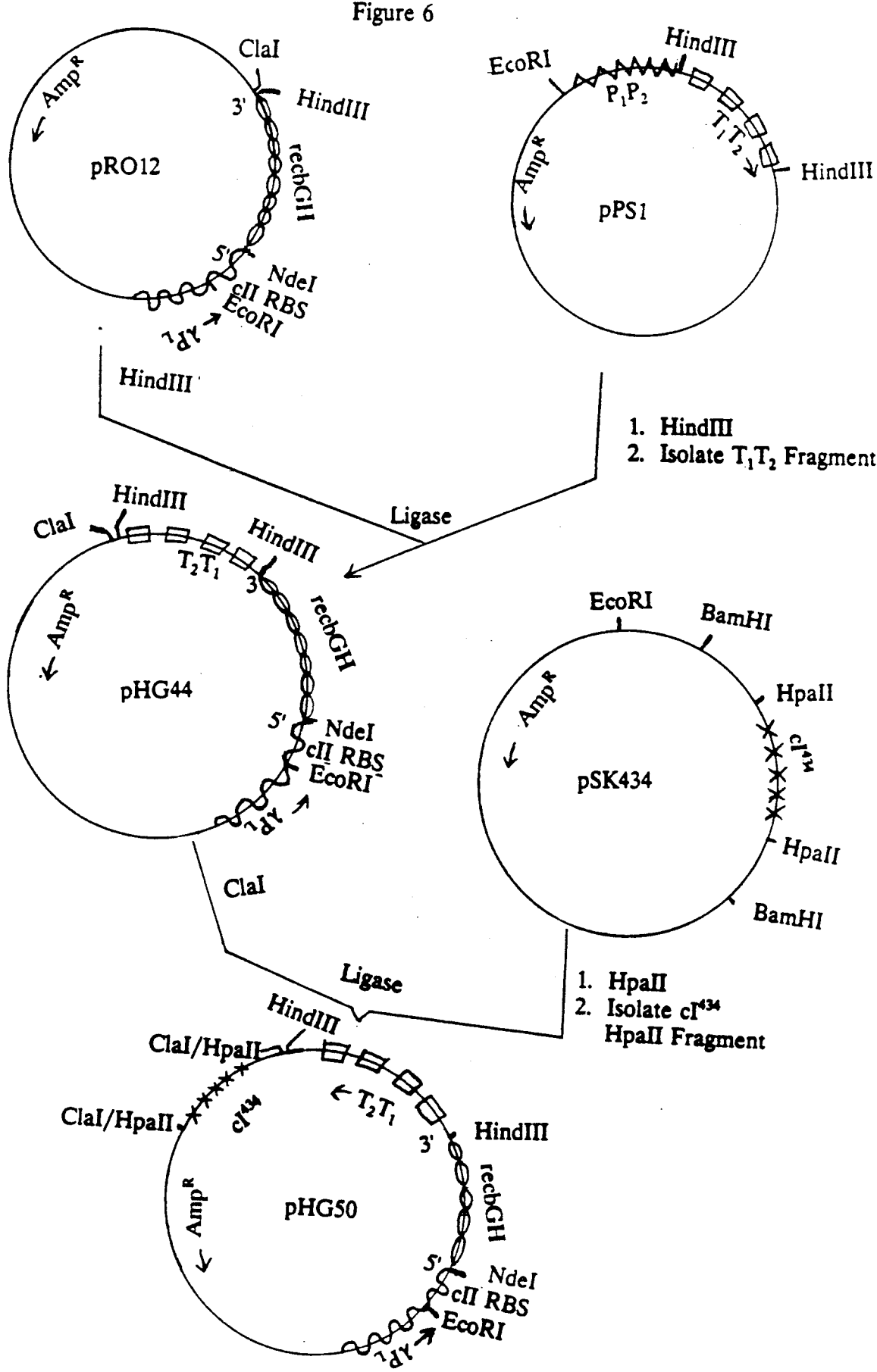

A1645 ($\lambda$i434cI$^-$ was derived by infecting *Escherichia coli* strain A1645 containing a plasmid with λimm434cI³⁰⁰⁸ mini Tn Δ16 Δ17 at 30° C. Tetracycline resistant colonies were isolated and purified. The strain containing plasmid pHG50 (FIG. 6) has been deposited with the American Type Culture Collection under ATCC No. 39805.

Preferably, the vector is a covalently closed circular double-stranded molecule. However, it is not essential that the vector be covalently closed.

The vector achieves its enhanced expression levels after the host cell is heated to a temperature at which the $C_I$ repressor protein is destroyed. A temperature above about 38° C. is effective for this purpose and since it is desired that unnecessary heat damage to the host cells be avoided to as great an extent as possible, it is generally desirable that the temperature not exceed 42° C. by more than a few degrees.

One important component of the vector is the ribosomal binding site. Suitable sites are $C_{II}$ from lambda bacteriophage having the sequence:

TAAGGAAATACTTACAT
ATTCCTTTATGAATGTA;

a mutant of $C_{II}$ from lambda bacteriophage having the sequence:

TAAGGAAGTACTTACAT
ATTCCTTCATGAATGTA;

the major head protein gene of bacteriophage lambda having the sequence:

TTTTTTTACGGGATTTTTTTATG
AAAAAAATGCCCTAAAAAAATAC;

the natural β-lactamase ribosomal binding site derived from pBR322;
a synthetic oligonucleotide having the sequence:

AATTCGAGCGCAAGGAAACAGGCTCA
   GCTCGCGTTCCTTTGTCCGAGTAT;

a synthetic oligonucleotide having the sequence:

AATTCAATAATATTGAAAAAGGAAGAG
   GTTATTATAACTTTTTCCTTCTCAT; and a natural ribosomal binding site derived from *Bacillus thurengensis*.

A DNA sequence which contains a gene associated with a selectable or identifiable phenotypic trait which is manifested when the vector is present in the host cell is also a component of the vector. Suitable genes include those associated with temperature sensitivity or drug resistance, e.g., resistance to ampicillin, chloroamphenicol or tetracycline.

Relative to vectors described previously, the vectors of this invention may be used to obtain enhanced expression of a wide variety of genes encoding desirable polypeptide products. Suitable genes include those encoding growth hormones, e.g., bovine, porcine, chicken or human growth hormones; superoxide dismutase; apoliprotein E or analogs of any of the preceding. By analog is meant a polypeptide having the same activity as the naturally occurring polypeptide but having one or more different amino acids added or deleted, or both, at the N-terminus of the polypeptide.

The vector may be formed by methods well known to those of ordinary skill in the art to which the invention relates. Such methods are described in greater detail in various publications identified herein, the contents of which are hereby incorporated by reference into the present disclosure in order to provide complete information concerning the state of the art.

One presently preferred vector is derived by removing the met—phe bGH gene from plasmid p830-10A. The plasmid has the restriction map shown in FIG. 7 and has been deposited in strain A2097 with the American Type Culture Collection under ATCC No. 39785.

Another presently preferred vector is derived by removing the rec bGH gene from plasmid pSAL-170/10. The plasmid has the restriction map shown in FIG. 8.

A third presently preferred vector is derived by removing the rec bGH gene from plasmid pSAL-210/4. The plasmid has the restriction map shown in FIG. 9.

The vectors of this invention, upon introduction into a host, may also be engineered to yield plasmids which produce analogs of bovine growth hormone. p830-10A (ATCC No. 39785), one example of such a plasmid, was constructed according to the scheme shown in FIG. 7. The analog it produces has a methionine residue added to the aminoterminus of the phenylalanine form of natural bGH.

Other plasmids produce analogs which have the amino acid sequence met—asp—gln added to N-terminus of the phenylalanine form of natural bGH. These .plasmids include pSAL-130/5 (FIG. 8), pSAL-170/10 (FIG. 8) and pSAL-210/4 (FIG. 9).

Using the same approach other plasmids may be prepared by inserting into the second restriction enzyme site of a vector according to the invention a gene encoding a desired polypeptide.

Various host vector systems involve *Escherichia coli* strains A1637, A1645, A2606, A2097 or A1563 if the plasmid does not contain the cI⁴³⁴ fragment and strain A1645 (λi434c⁻ mini Tn10) if the plasmid contains the cI⁴³⁴ fragment. The host vector systems and plasmid described herein may be used to produce different polypeptides such as bovine, porcine, chicken and human growth hormones, human superoxide dismutase and human apolipoprotein E. To do so, the host vector system is grown under suitable conditions permitting production of polypeptide which is then recovered.

Suitable conditions involve growth of the host vector system for an appropriate period of time at about 42° C. Desirably, the period of growth at 42° C. is about 1 to 5 hours. Suitable media include casein hydrolysate.

Veterinary compositions may be prepared which contain effective amounts of bGH analog and a suitable carrier. Such carriers are well known to those of ordinary skill in the art. The analogs may be administered directly or in the form of a composition to a cow in order to increase milk or meat production.

EXAMPLES

The examples which follow are set forth to aid in understanding the invention but are not intended to, and should not be construed to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well known to those of ordinary skill in the art and are described in numerous publications including by way of example the following:

J. Miller, *Experiments in Molecular Genetics*, Cold Spring Harbor Laboratory, New York (1972).

T. Maniatis, E. F. Fritsch and J. Sambrook, *Molecular Cloning; A Laboratory Manual*, Cold Spring Harbor Laboratory, New York (1982).

*Methods in Enzymology*, vol. 65, "Nucleic Acids (Part 1)," edited by Lawrence Grossman and Kivie Moldave, Academic Press, New York (1980).

*Methods in Enzymology*, vol. 68, "Recombinant DNA," edited by Ray Wu, Academic Press, New York (1981).

*Methods in Enzymology*, vol. 100, "Recombinant DNA (Part B)," edited by Ray Wu, Lawrence Grossman and Kivie Moldave, Academic Press, New York (1983).

Methods in Enzymology, vol. 101, "Recombinant DNA (Part C)," edited by Ray Wu, Lawrence Grossman and Kivie Mold ave, Academic Press, New York (1983).

*Principles of Gene Manipulation, An Introduction to Genetic Engineering*, 2nd Edition, edited by R. W. Old and S. B. Primrose, University of California Press (1981).

H. V. Bernard, et al., Gene (1979) 5, 59.

A. B. Oppenheim, et al., J. Mol. Biol. (1982) 158, 327.

E. Remaut, et al., Gene (1981) 15, 81.

EXAMPLE 1 p830-10A

The construction of p830-10A (ATCC No. 39785) is shown in FIG. 7 and is described in the Description of the Figures. The plasmid p830-10A was derived from the constitutive high copy number plasmid pOP1Δ6 (Gelfand, D. H., et al., PNAS (1978) 75, 5869; Meusing, et al., Cell (1981) 24, 235–242). p7200-22, also shown in FIG. 7, was digested with ClaI and the ClaI-ClaI fragment, which contains the $\lambda P_L$ promoter, the bGH gene and the $T_1T_2$ sequences was isolated. The ClaI-ClaI fragment was inserted into the unique ClaI site of pOP1Δ6. (The plasmid p7200-22 is a derivative of pSAL 5600-1 (FIG. 10) in which a synthetic ClaI linker was introduced at the BglII site "upstream" of the $\lambda P_L$ promoter.)

Plasmid p830-10A was found to maintain the constitutive high copy number phenotype even after induction of the $\lambda P_L$ promoter at about 42° C. This may be due to the presence of the $T_1T_2$ termination sequences at the 3′ end of the bGH sequence which prevents formation of long mRNA transcripts from the $\lambda P_L$ promoter which might interfere with other mRNA transcripts at the origin of replication of pOP1Δ6.

p830-10A was introduced into Escherichia coli strain A2097 by transformation using methods known to those of ordinary skill in the art. This strain produces upon growth and induction an analog of bovine growth hormone having a methionine residue added to the amino terminus of the phenylalanine form of natural bGH. The amount of bGH analog produced was about 37–43% of the total protein produced by the bacteria as calculated by scanning Coomasie-stained SDS polyacrylamide gels. The methods used to grow the strain, recover the bGH analog produced and purify the bGH analog, are the same as those described for pSAL-170/10 in Example 5.

TABLE I[1]

| Plasmid | % bGH[2] | Remarks |
| --- | --- | --- |
| pRec 2/3 | 23 | $Amp^R$ |
| pRO11 | 28 | $Amp^R$ |
| pRO12 | 30–36 | $Amp^R$ |
| pHG44 | 37–42 | $Amp^R, T_1T_2$ |
| pHG50 | 37–42 | $Amp^R, T_1T_2; cI^{434}$ |
| pSAL-130/5 | 39–44 | $Amp^R; CHCN; T_1T_2$ |
| pSAL-170/10 | 40–46 | $Tet^R; CHCN; T_1T_2$ |

[1]The table summarizes the bGH expression levels of various plasmids derived from pRO211. The plasmids pRec 2/3 and pRO11 are described in copending, coassigned U.S. Pat. application Ser. No. 514,188, filed July 15, 1983.
[2]Amount of bGH produced as percentage of total bacterial protein.
ABBREVIATIONS
CHCN = Constitutive high copy number
$Amp^R$ = Ampicillin resistance
$Tet^R$ = Tetracycline resistance
$T_1T_2$ = Transcription termination sequences
$cI^{434}$ = Plasmid stabilization $cI^{434}$ system

EXAMPLE 2

A general utility expression vector may be derived from the plasmid p8300-10A (FIG. 7, ATCC No. 39785) by excision of the bGH gene. A vector so derived has numerous advantages over previously described expression vectors including:

1. Extremely High Levels of Expression

The vector is capable of directing expression of foreign proteins in *Escherichia coli* at levels as high as 44% of the total cellular protein. constitutive high copy number

2. Constitutive High Copy Number

The vector maintains a constitutively high copy number of about 200–300 copies per cell. This is in distinction to other $\lambda P_L$ expression vectors which are present in lower copy numbers. The high copy number contributes to higher levels of expression.

3. Transcription Termination Signals

The vector which may be obtained by excision of bGH sequence from p8300-10A contains the $T_1T_2$ transcription termination signals placed "downstream" from the $\lambda P_L$ promoter and $C_{II}$ ribosomal binding site. The high levels of expression are due in part to the presence of the $T_1T_2$ transcription terminators at the end of the inserted gene transcription of N-modified RNA polymerase. Thus the transcription terminators prevent the $\lambda P_L$ -controlled transcription of undesired plasmid proteins, thereby enhancing the relative yields of the desired protein. Furthermore the presence of the $T_1T_2$ transcription termination signals prevents long mRNA transcripts through the plasmid origin of replication. This enhances the stability of the high copy phenotype.

Similar high copy number plasmids containing the $\lambda P_L$ promoter but lacking the transcription termination sequences are unstable and tend to lose the high copy number phenotype.

4. Replaceable Ribosomal Binding Site p8300-10A contains a unique EcoRI site which is located "upstream" of the ribosomal binding site, and an NdeI site located "downstream" of the ribosomal binding site. Thus, the ribosomal binding site is bounded by two unique restriction sites. This enables facile excision of the present ribosomal binding site (the $\lambda C_{II}$ ribosomal binding site) and substitution of virtually any other natural or synthetic ribosomal binding site without altering other features of the plasmid. This greatly facilitates optimal expression of desired polypeptides.

5. Thermoinducible Regulation of Expression

The λP$_L$ promoter is inactive when the C$_I$ repressor is bound to it. The cI857 repressor is thermosensitive, that is, it binds to the promoter at 30° C. but is inactivated at 42° C. Thus, by increasing the temperature of fermentation to 42° C. the host bacteria are induced to produce the desired protein.

The advantages of such a system include the following:

(a) A foreign protein which is toxic to *Escherichia coli* can be produced late in the fermentation
   process thus avoiding early cell death, (b) Overproduction of a protein may stabilize the protein and prevent proteolytic degradation. (Cheng, Y. E., et al., Gene (1981) 14, 121).

Thus, "instantaneous" overproduction using a tightly regulated promoter such as λP$_L$ may be preferable to continuous low level production.

6. Simplified Induction Protocol

Protein production by the plasmids described in this patent application and in copending, coassigned U.S. patent application Ser. No. 514,188 is regulated by the thermosensitive cI$^{857}$ repressor.

The induction protocol required by the plasmids described in the copending, coassigned application involved induction at 42° C. followed by growth at 38° C. In contrast, the optimal induction of protein synthesis when using the plasmid p8300-10A or pSAL-130/15 or their plasmid derivatives involved induction at 42° C. followed by growth at the same temperature, i.e., 42° C. This eliminates the need to cool the fermentor.

7. Ribosome Binding Site and Initiation Codon

This expression vector contains a strong procaryotic ribosomal binding site (RBS) as well as a translation initiation codon (ATG). Thus, any eucaryotic gene may be cloned without adding the initiation codon. Furthermore, the efficient RBS increases levels of expression. The ribosome binding site is the λ C$_{II}$ ribosomal binding site. The sequence of the ribosomal binding site is:

```
TAAGGAAGTACTTACAT
ATTCCTTCATGAATGTA
```

One base pair is different from the ribosomal binding site found in the wild type λ.

8. Convenient Restriction Site

The expression vector has a unique NdeI restriction site which contains within the site the ATG initiation codon. This permits proper positioning of the desired gene. The unique NdeI site is found immediately after the ribosomal binding site.

9. Nut Site

N protein, which is provided by the host, binds the Nut site on the expression vector and thereby prevents termination of transcription at the tRI site or premature transcription termination within the cloned gene.

Strains

Suitable hosts for the described vectors and plasmids are strains of *Escherichia coli* suitable for transformation, including A1637, A2602, A1563, A1645 (c600 r$^-$m$^+$ gal$^+$ thr$^-$ leu$^-$ lac$^-$ b1 (λcI$^{857}$ ΔH1 ΔBamHI N$^+$)) and A2097 (A1645 lac ΔχA21 proC::Tn 10).

EXAMPLE 3 pSAL-130/5

The construction of pSAL-130/5 is shown in FIG. 8 and described in the Description of the Figures. pSAL-130/5 was obtained from p8300-10A (ATCC No. 39785) by replacing the met—phe bGH gene with the met—asp—gln bGH gene. The met—asp—gln bGH gene was obtained from plasmid pHG44 (FIG. 6) (ATCC No. 39806) by NdeI and HindIII digestion.

pSAL-130/5 was introduced into *Escherichia coli* strain A1645 by transformation using methods known to those of ordinary skill in the art. This strain produces upon growth and induction an analog of bovine growth hormone (bGH) having the amino acid sequence met—asp—gln added to the N-terminus of the phenylalanine form of natural bGH. The amount of bGH analog produced by pSAL-130/5 was about 39–44% of the total protein produced by the bacteria as calculated by scanning Coomasie blue-stained SDS polyacrylamide gels (Table I). The methods used to grow the strain, recover the bGH analog produced and purify the bGH analog are the same as those described for pSAL-170/10 in Example 5.

EXAMPLE 4 pSAL-170/10

The construction of pSAL 170/10 is shown in FIG. 8 and described in the Description of the Figures.

pSAL 170/10 was introduced into *Escherichia coli* strain A1645 by transformation using known methods. This strain produces upon growth and induction an analog of bGH having the amino acid sequence met—asp—gln added to the amino terminus of the phenylalanine form of natural bGH. The amount of the bGH analog produced by pSAL-170/10 was about 40–46% of the total protein produced by the bacteria as calculated by scanning the Coomasie-stained SDS polyacrylamide gels. (Table I).

EXAMPLE 5

Growth of pSAL-170/10

I. Stock Cultures

Stock cultures of pSAL-170/10 were grown on casein medium (see Inoculum), then diluted two-fold with freezing medium and stored at −80° C. Freezing medium contains per 500 ml:

| | |
|---|---|
| K$_2$HPO$_4$ | 6.3 gr |
| KH$_2$PO$_4$ | 1.8 gr. |
| Na Citrate | 0.45 gr |
| MgSO$_4$.7H$_2$O | 0.09 gr |
| (NH$_4$)$_2$SO$_4$ | 0.9 gr |
| Glycerol | 44.0 gr |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C. and approximately 200 r.p.m. As needed subsequent stages in inoculum propagation were carried our in stirred aerated fermenters. Sterile medium was inoculated with 2-10% inoculum and incubated 15 hours at 30° C., pH 7±0.5 with agitation and aeration to maintain a dissolved oxygen level above 20% air saturation.

III Production

7 The production medium contains:

| Casein hydrolysate | 20 g/l |
| Yeast extract | 10 g/l |
| K₂HPO₄ | 2.5 g/l |
| MgSO₄.7H₂O | 1 g/l |
| NaCl | 5 g/l |
| Biotin | 0.1 mg/l |
| Thiamine | 1 mg/l |
| Trace elements solution | 3 ml/l |

The medium also contains 12.5 mg/liter tetracycline. The tetracycline is optional for production but is always found in the medium used for growing the inoculum.

Biotin, thiamine and antibiotics in concentrated solution were filter sterilized separately and added to the sterile production medium before inoculation. Sterile glucose solution was added initially to supply 10 g/l. At the induction step another 10 g/l of glucose was added.

The trace elements solution contains

| FeCl₃ | 16 g/l |
| ZnCl₂.4H₂O | 2 g/l |
| CoCl₂.6H₂O | 2 g/l |
| Na₂MoO₄.2H₂O | 2 g/l |
| CaCl₂.2H₂O | 1 g/l |
| CuCl₂ | 1 g/l |
| H₃BO₃ | 0.5 g/l |
| Conc. HCl | 100 ml/l |

The medium is inoculated with 0.5-10% inoculum culture and incubated at 30° C. Agitation-aeration rates are set to maintain a dissolved oxygen level above 20% air saturation. The pH is maintained at 7±0.2 with $NH_3$. Once cell concentration reaches about 3.5 g/l ($OD_{660}=10$) induction is started.

The temperature is raised to 42° C. and maintained at 42° C. for 1-5 hours. The culture is then chilled and cells are recovered by centrifugation for hormone purification.

Recovery of bGH

Thirteen kilograms of bacterial cells (wet cake) are resuspended in 5 volumes of a solution containing 50 mM sodium phosphate buffer (pH 7.4), 50 mM EDTA and 100 mM NaCl, using a Polytron (Kinematica) blender, while controlling the blender's speed to minimize foaming. The homogenous suspension is continuously passed through a Dynomill cell disruptor KD5 (Willy A. Bachofen, Basel) at a rate of 80 liter per hour and the homogeneous suspension of disrupted cells clarified by centrifugation in a CEPA 101 centrifuge at a flow rate of 45 liter per hour. The precipitate from the centrifugation step is collected and resuspended in 15.5 liters of 50 mM sodium phosphate buffer (pH 7.4) containing 50 mM EDTA. Lysozyme is added to a final concentration of 0.05 mg/ml and the suspension incubated for 16 hours at 37° C. Triton X-100 is added to a final concentration of 1%. The suspension is then incubated for 30 minutes at room temperature, sonicated in a continuous flow cell sonificator (Heat System) at a rate of 18 liters per hour and centrifuged in a CEPA 101 centrifuge. The precipitate is collected, resuspended in 50 mM sodium phosphate buffer (pH 7.4), sonicated as above, and centrifuged in a CEPA 101 centrifuge. The cells are resuspended in 15.5 liters of 50 mM sodium phosphate buffer (pH 7.4) containing 50 mM EDTA and 100 mM NaCl and twice precipitated and resuspended in 15.5 liters of distilled water. The precipitate is collected by centrifugation and stored at −20° C.

Purification Of bGH

The precipitate is resuspended in 30–40 liters distilled water and solubilized by titration with 0.5N NaOH to pH 11.8. The solution is then continuously sonicated and clarified by centrifugation in CEPA 101 centrifuge if necessary, or filtered through Whatman No. 1 paper.

The clarified protein solution (32.6 liters containing 297,000 OD's at 280 nm) is divided into separate portions (6×5.4 liters) each containing 50,000-60,000 OD's. Each portion is ultrafiltered separately through a Millipore Pellicon ultrafilter equipped with three 100,000 molecular weight cutoff cassettes (type PTHK) of 5 ft² area each. A 5.4 liter portion is concentrated to 1 liter retentate volume. The ultrafiltrate is collected and saved. The retentate is diluted back to its original volume with fresh 10 mM Borate buffer, pH 11.8, and mixed well. The batch is concentrated again to 1 liter retentate volume. The ultrafiltrate is collected and combined with the first ultrafiltrate. When the running total of the OD's in the ultrafiltrates equals 20% of the OD's initially charged to the ultrafilter, the retentate volume on the next concentration step is taken to 0.5 liters instead of 1 liter. The cycle of concentration and dilution with 10 mM Borate buffer is continued until the ultrafiltrate from a retentate volume of 0.5 liters has an absorbance at 280 nm (1-cm cell) of less than 0.1. This normally takes between 9 and 12 cycles of concentration and dilution. The final retentate is discarded.

All ultrafiltrates are combined and adjusted to pH 9.0 with 6N HCl. The other 5.4-liter portions are ultrafiltered in the same fashion, and all pH adjusted ultrafiltrates are combined. A typical run produces a total of 380 liters of ultrafiltrates with an absorbance of 0.26 equivalent to 100,000 OD's and requires 24 to 40 hours to complete.

The combined ultrafiltrates (380 liters containing 100,000 OD's at 280 nm) from the 100K ultrafiltration step are loaded onto a Sepharose CL-6B DEAE ion-exchange column at a linear flow velocity of 23 cm/hr (25 liter/hr). The 37-cm diameter 15-cm high column is washed with two bed volumes (32 L) of 10 mM Borate buffer at pH 9.0. The eluate from the loading and washing steps is discarded. A step change in eluent to 10 mM Borate, 100 mM sodium chloride, pH 9, displaces the bGH off the column. The elution flow velocity is 23 cm/hr. The progress of the run is monitored by following absorbance of the eluate at 280 nm. The bGH peak is collected in 4 to 5 bed volumes (84 liters containing 43,000 OD's at 280 nm) and then concentrated to approximately 10 mg/ml using a Millipore Pellicon ultrafiltration device with a 10,000 molecular weight cutoff cassettes. The solution is then lyophilized. The yield is approximately 70 g of pure bGH.

EXAMPLE 6

Activity Of bGH Analog Produced By pSAL-170/10

1. Radioimmunoassay Comparison of bGH Analog with Natural bGH

A solution containing 100 ng/ml bGH analog was prepared in phosphate buffered saline (1% BSA). This solution was diluted serially to concentrations of 50, 25, 12.5, 6.25, 3.12, 1.56 and 0.78 ng/l. Duplicate 0.1 ml aliquots of these solutions were submitted to RIA using a double antibody procedure. The dilution curve was comparable to that obtained with natural bGH.

2. Radioreceptor Binding Assay

A radioreceptor binding assay was performed with rabbit liver membranes as described by Tushima, T. and Freisen, H. G., (Y. Chin., Endocr. Metab. (1973), 37; 3) using $^{125}$I-bGH as the tracer and authentic bGH solutions for the construction of calibration curves. Samples were incubated in triplicate for two hours at room temperature in 0.3 ml of assay buffer (50 mM Tris, 15 mM $CaCl_2$ and 5 mg/ml bovine serum albumin, pH 7.6). The tubes contained $^{125}$I-bGH (20,000 cpm of preparation of 30–60 μci/μg), 150–250 μg liver membrane protein and either natural bGH (1–100 ng) or extracts of bacterial bGH. The result demonstrated that the bGH activity of the bGH analog is comparable to that of natural bGH.

3. Tibia Test

The bioactivity of the pRO12 produced bGH analog recovered from bacterial cells according to Example 5 was evaluated by a tibia test. (Parlow, A. F., et al., Endocrinology (1965) 77:1126). Rats were hypophysectomized at 28–30 days of age, then kept for 10–14 days without treatment. Bovine growth hormone derived from bovine pituitaries or from recombinant *Escherichia coli* was dissolved in 0.15M NaCl+0.01M borate, pH 10.0. Rats (4–7 per group) received daily subcutaneous injections of bGH solutions (5–125 μg/day in 0.2 cc) for 5 days while kept on a normal diet (Purina Rat-Chow and water adlibitum). The animals were sacrificed on the 6th day, their foreleg knee-bones taken out, cut longitudinally, fixed with acetone and stained with 2% $AgNO_3$. The width of the epiphyseal plates was measured by observation through a dissecting binocular (Nikon). Mean values (40 readings per rat) were used for the construction of long dose-response curves. The results demonstrated that the bGH activity of the pSAL-170/10-produced bGH analog is comparable to that of natural bGH.

What is claimed is:

1. A plasmid for production of a bovine growth hormone polypeptide analog having the amino acid methionine attached to the N-terminus of the phenylalanine form of the naturally-occurring polypeptide, said analog having substantially the same biological activity as the naturally-occurring polypeptide, designated p8300-10A having the restriction map shown in FIG. 7 and deposited under ATCC Accession No. 39785.

2. A plasmid for production of a bovine growth hormone polypeptide analog having the amino acids methionine, aspartic acid and glutamine attached to the N-terminus of the naturally-occurring polypeptide, said analog having substantially the same biological activity as the naturally-occurring polypeptide, designated pSAL-130/5 having the restriction map shown in FIG. 8.

3. A plasmid for production of a bovine growth hormone polypeptide analog having the amino acids methionine, aspartic acid and glutamine attached to the N-terminus of the naturally-occurring polypeptide, said analog having substantially the same biological activity as the naturally-occurring polypeptide, designated pSAL 170/10 having the restriction map shown in FIG. 8.

4. A host plasmid system for production of met—phe bovine growth hormone having the amino acid methionine attached to the N-terminus of the phenylalanine form of the naturally-occurring polypeptide which comprises the plasmid of claim 1 in a suitable *E. coli* host.

5. A host plasmid system of claim 4, wherein the *Escherichia coli* host strain is selected from the group consisting of strain A1637, A1645, A2602, A2097 or A1563.

6. A method for producing bovine growth hormone polypeptide analog which comprises growing the hose plasmid system of claim 4 under suitable conditions permitting production of the bovine growth hormone polypeptide analog and recovering the resulting bovine growth hormone analog.

7. A hose plasmid system for production of bovine growth hormone analog having the amino acids methionine, aspartic acid and glutamine attached to the N-terminus of the naturally-occurring polypeptide which comprises the plasmid of claims 2 or 3 in a suitable *E coli* host.

8. A host plasmid system of claim 7, wherein the *Escherichia coli* host strain is selected from the group consisting of strain A1637, A1645, A2602, A2097 or A1563.

9. A method for producing bovine growth hormone polypeptide analog which comprises growing the hose plasmid system of claim 7 under suitable conditions permitting production of the bovine growth hormone polypeptide analog and recovering the resulting bovine growth hormone analog.

* * * * *